US006982318B1

(12) United States Patent
Comb et al.

(10) Patent No.: US 6,982,318 B1
(45) Date of Patent: Jan. 3, 2006

(54) PRODUCTION OF MOTIF-SPECIFIC AND CONTEXT-INDEPENDENT ANTIBODIES USING PEPTIDE LIBRARIES AS ANTIGENS

(75) Inventors: Michael J. Comb, Manchester, MA (US); Yi Tan, Lynnfield, MA (US)

(73) Assignee: Cell Signaling Technology, Inc., Beverly, MA (US)

( * ) Notice: Subject to any disclaimer, the term of this patent is extended or adjusted under 35 U.S.C. 154(b) by 0 days.

(21) Appl. No.: 09/535,364

(22) Filed: Mar. 24, 2000

Related U.S. Application Data

(63) Continuation-in-part of application No. 09/148,712, filed on Sep. 4, 1998, now Pat. No. 6,441,140.

(30) Foreign Application Priority Data

Aug. 26, 1999 (WO) .............................. PCT/US99/19597

(51) Int. Cl.
*C07K 16/18* (2006.01)

(52) U.S. Cl. ............................... 530/387.1; 530/388.1; 530/389.1

(58) Field of Classification Search .............. 530/387.1, 530/388.1, 389.1
See application file for complete search history.

(56) References Cited

U.S. PATENT DOCUMENTS

| | | | |
|---|---|---|---|
| 5,532,167 A | | 7/1996 | Cantley et al. |
| 5,759,787 A | * | 6/1998 | Strulovici ................... 435/7.4 |
| 6,001,580 A | * | 12/1999 | Tani et al. ................... 435/7.1 |

OTHER PUBLICATIONS

Miceli et al. J. Immunological Methods 167 :279–287 (1994).*
Karin, Curr. Opin. Cell Biol. 6:415–424 (1994).
Lewis et al., Adv. Cancer Res. 74:49–139 (1998).
Crowley et al., Cell 77:841–852 (1994).
Fukunaga et al., EMBO 16(8):1921–1933 (1997).
Stukenberg et al., Curr. Biol. 7:338–348 (1997).
Burbelo et al., Curr. Biol. 5(2):95–96 (1995).
Yaffe et al., Cell 91:961–971 (1997).
Muslin et al., Cell 84:889–897 (1996).
Struhl, Genes & Dev. 12:599–606 (1998).
Imhof et al., Curr. Biol. 7:689–692 (1997).
Ross et al., Nature 294:654–656 (1981).
Kozma et al., Method. Enzymol. 201:28–43 (1991).
White et al., Method. Enzymol. 201:65–79 (1991).
Kamps, Method. Enzymol. 201:101–111 (1991).
Frackelton et al., Method. Enzymol. 201:79–92 (1991).
Wang, Method. Enzymol. 201:53–65 (1991).
Glenney, Method. Enzymol. 201:92–100 (1991).
Heffetz et al., Method. Enzymol. 201:44–53 (1991).
Czernik et al., Method. Enzymol. 201:264–283 (1991).
Czernik et al., Neuroprot. 6:56–61 (1995).
Patterson & Garrels, Cell Biology: A Laboratory Handbook 249–257 (1994), Academic Press.
Fields et al., Pept. Res. 4:95–101 (1991).
Dourtoglou et al., Synthesis 1984:572–574 (1984).
Knorr et al., Tetra. Let. 30:1927–1930 (1989).
Kearney et al., J. Immunol. 123:1548–1550 (1979).
Verhoeven, et al. Science 239:1534–1536 (1988).
Reichmann, et al., Nature (England) 332:323–327 (1988).
Huse, et al., Science 246:1275–1281 (1989).
Knorr, et al., Peptides 1988:37–39 (1989).
Hamaguchi, et al., Molecular & Cellular Biology 8:3035–3042 (1988).
Sigma 1998 Catalog pp. 1305 and 1309.
Upstate Biotechnology 1998 Catalog p. 17.
Zymed Laboratories 1996–1997 General Catalog p. 80.
Monoclonal Antibodies, Hybridomas: A New Dimension in Biological Analyses, Kennett et al. (eds.), Plenum Press (1980).
Antibodies: A Laboratory Manual, Harlow and Lane (eds.), Cold Spring Harbor Laboratory Press (1988).
Methods in Enzymology, vol. 201, Protein Phosphorylation, Part B Analysis of Protein Phosphorylation, Protein Kinase Inhibitors and Protein Phosphatases, Hunter and Sefton (eds.), Academic Press, Inc. (1991), pp. 3–547
Alessi, et al., FEBS Lett. 399:333–338 (1996).
Franke, et al. Cell 88:435–437 (1997).
Pap, et al., Biol. Chem. 273:19929–19932 (1998).
Datta, et al., Cell 91:231–241 (1997).
Brunet, et al., Cell, 96:857–868 (1999).
Cardone, et al., Science, 282:1318–1321 (1998).
Montminy, Annual Rev. Bochem. 66:807–822 (1997).
Songyang, et al., Current Biology 4:973–982 (1994).
Alessi, et al., EMBO J. 15:6541–6551 (1996).
Dalby, et al., J. Biol. Chem. 273:1496–1505 (1998).
Keranen, et al., Curr. Biol., 5:1395–1403 (1995).
Peng, et al., Science, 277:1501–1508 (1997).
Zha, et al., Cell 87:619–628 (1996).
Westendorf, PNAS, 91:714–718 (1994).
Rosenberg, et al., Journal of Biological Chemistry 268:4499–4503 (1993).
Kushima, et al., Journal of Molecular Neuroscience 8:19–27 (1997).
Yaffe, et al., Science 278:1957–1960 (1997).

* cited by examiner

*Primary Examiner*—Karen A. Canella
(74) *Attorney, Agent, or Firm*—James Gregory Cullem

(57) ABSTRACT

A class of motif-specific, context-independent antibodies that bind conserved signal transduction motifs, such as kinase consensus substrate motifs and protein-protein binding motifs, containing one or more modified amino acids, such as a phosphorylated amino acid, is provided. The antibodies bind a plurality of peptides or proteins that contain the modified motif. Context-independent antibodies specific for single modified residues, such as phosphothreonine, are also provided. Methods for producing and using such antibodies are provided.

11 Claims, 17 Drawing Sheets

FIG. 1A

| PEPTIDE | SEQUENCE | ANTIBODY DILUTIONS | | | | | | | |
|---|---|---|---|---|---|---|---|---|---|
| | | 1.00E+03 | 5.00E+03 | 1.00E+04 | 5.00E+04 | 1.00E+05 | 5.00E+05 | 1.00E+06 |
| Thr* | x-x-x-x-x-Thr*-x-x-x-x-x-Cys | 1.92 | 1.32 | 0.54 | 0.34 | 0.07 | 0.04 | 0.02 |
| Ser-Thr | x-x-x-x-x-x-Ser/Thr-x-x-x-x-x-Cys | 0.11 | 0.05 | 0.01 | 0.00 | 0.01 | 0.00 | 0.00 |
| Threonine* mix | 18 phospho-Thr peptide | 1.84 | 1.13 | 0.40 | 0.26 | 0.10 | 0.07 | 0.05 |
| Serine* mix | 38 phospho-Ser peptide | 0.12 | 0.04 | 0.02 | 0.02 | 0.02 | 0.01 | 0.00 |
| Akt-Thr308-P | Ile-Lys-Asp-Gly-Ala-Thr-Met-Lys-Thr*-Phe-Cys-Gly-Thr-Pro (SEQ ID NO:1) | 1.15 | 0.65 | 0.24 | 0.13 | 0.03 | 0.01 | 0.00 |
| APP1-Thr668-P | Asp-Ala-Ala-Val-Thr*-Pro-Lys-Lys-Arg-His-Leu-Ser-Lys-Cys (SEQ ID NO:2) | 0.14 | 0.03 | 0.01 | 0.01 | 0.01 | 0.01 | 0.00 |
| C-P | Asp-Thr-Gln-Ile-Lys-Arg-Asn-Thr*-Phe-Val-Gly-Thr-Pro-Phe-Cys (SEQ ID NO:3) | 1.71 | 1.13 | 0.39 | 0.22 | 0.03 | 0.02 | 0.02 |
| CAK-Thr167-P | His-Gln-Val-Val-Thr*-Arg-Trp-Tyr-Arg-Cys (SEQ ID NO:4) | 1.77 | 1.15 | 0.41 | 0.27 | 0.08 | 0.03 | 0.01 |
| CAMIV-Thr196-P | His-Gln-Val-Leu-Met-Lys-Thr*-Val-Cys-Gly (SEQ ID NO:5) | 1.79 | 1.38 | 0.63 | 0.40 | 0.09 | 0.05 | 0.01 |
| CDC2-Thr167-P | Ile-Pro-Ile-Arg-Val-Tyr-Thr*-His-Glu-Val-Val-Thr-Leu-Cys (SEQ ID NO:6) | 1.02 | 0.56 | 0.14 | 0.08 | 0.03 | 0.01 | 0.01 |
| CDK2-Thr159-P | Gly-Val-Pro-Val-Arg-Thr-Tyr-Thr*-His-Glu-Val-Val-Thr-Leu-Cys (SEQ ID NO:7) | 1.66 | 1.79 | 0.51 | 0.44 | 0.08 | 0.04 | 0.02 |
| p70S6K-Thr389-P | Asn-Gln-Val-Phe-Leu-Gly-Phe-Thr*-Tyr-Val-Ala-Pro-Lys-Lys-Cys (SEQ ID NO:8) | 1.99 | 1.44 | 0.62 | 0.39 | 0.08 | 0.04 | 0.01 |
| PKCalpha-P | Lys-Glu-His-Ala-Met-Asp-Gly-Val-Thr-Thr-Arg-Thr*-Phe-Cys (SEQ ID NO:9) | 1.82 | 1.63 | 0.94 | 0.68 | 0.18 | 0.08 | 0.02 |
| ERK-P | Asp-His-Thr-Gly-Phe-Leu-Thr*-Glu-Tyr*-Val-Ala-Thr-Arg-Trp-Cys (SEQ ID NO:10) | 1.56 | 1.18 | 0.51 | 0.30 | 0.07 | 0.04 | 0.02 |
| Myc Ser54/62-P | Glu-Leu-Leu-Pro-Thr*-Pro-Pro-Leu-Ser*-Pro-Ser-Arg-Arg-Ser-Cys (SEQ ID NO:11) | 0.11 | 0.05 | 0.03 | 0.02 | 0.02 | 0.02 | 0.02 |
| P38-2P | Leu-Ala-Arg-His-Thr-Asp-Asp-Glu-Met-Thr*-Gly-Tyr*-Val-Val-Thr-Arg-Tyr-Arg-Cys (SEQ ID NO:12) | 0.54 | 0.30 | 0.08 | 0.06 | 0.04 | 0.04 | 0.02 |
| JNK-2P | Ser-Phe-Met-Met-Thr*-Pro-Tyr*-Val-Val-Thr-Arg-Tyr-Tyr-Arg-Cys (SEQ ID NO:13) | 1.49 | 0.44 | 0.12 | 0.07 | 0.03 | 0.02 | 0.02 |

FIG. 1B

| PEPTIDE SEQUENCE | phospho-Thr Reactivity |
|---|---|
| XXXXXXS*XXXXXX | — |
| XXXXY*XXXX | — |
| XXXXXPXS*/T*PXR/KXXX (SEQ ID NO:14) | + + |
| XXXXRSXS*XPXXXX (SEQ ID NO:15) | — |
| XXXXRSXSXPXXXX (SEQ ID NO:16) | — |
| XXXXXPXS*/T*PXXXXX (SEQ ID NO:17) | + + |
| XXXXXPXS/TPXXXXX (SEQ ID NO:18) | — |
| XXXXXT*XXXXXX | + + + |
| XXXXXXS/TXXXXXX | — |
| 21 phospho-Thr peptides mixture | + + + |
| 38 phospho-Ser peptides mixture | — |
| 30 phospho-Tyr peptides mixture | — |
|  |  |
| NEB LIBRARY |  |
| X-X-X-X-D/E-X-X-S*-T*-X-X-X-X-X-C (SEQ ID NO:19) | + + + |
| X-X-X-X-X-X-S*/T*-D/E-D/E-D/E-X-X-X (SEQ ID NO:20) | + + |
| X-X-X-X-F-X-X-F-S*/T*-F/Y-X-X-X-X-C (SEQ ID NO:21) | + + + |
| X-X-X-X-R/K-X-S*/T*-X-X-X-X-X-X-C (SEQ ID NO:22) | + + + |
| X-X-X-R/K-X-X-S*/T*X-X-X-X-X-X-C (SEQ ID NO:23) | + + + |
| X-X-X-X-X-X-S*/T*-F/I/M-X-X-X-X-X-C (SEQ ID NO:24) | + + + |
| X-X-X-X-X-X-S*/T*-F/I-X-X-X-X-X-C (SEQ ID NO:25) | + + + |
| X-X-X-X-X-X-S*/T-P-X-X-X-X-X-X-C (SEQ ID NO:26) | + + |
| X-X-X-X-X-T*-X-X-X-X-X-X-C | + + + |
| X-X-X-X-X-P-X-S*/T*-P-X-X-X-X-X-C (SEQ ID NO:27) | + + |
| X-X-X-X-X-X-S/T-X-X-X-X-X-X-C (SEQ ID NO:28) | — |
| X-X-X-X-X-P-X-S*/T*-P-X-R/K-X-X-X-C (SEQ ID NO:29) | + + |
| ANTIBODY REACTIVITY | ELISA O.D. |
| + + +   very strong | > 2 |
| + +   strong | 1 – 2 |
| +   weak | 0.2 – 1 |
| —   very little | < 0.2 |

FIG. 1D

Fixed AA position relative to phospho-Ser*/Thr*

| Fixed Amino Acid | -4 | -3 | -2 | -1 | S*/T* | +1 | +2 | +3 |
|---|---|---|---|---|---|---|---|---|
| Ala | +++ | ++ | ++ | +++ |  | +++ | +++ | ++ |
| Cys | +++ | +++ | +++ | +++ |  | +++ | +++ | ++ |
| Asp | ++ | ++ | ++ | +++ |  | +++ | +++ | ++ |
| Glu | ++ | ++ | ++ | +++ |  | +++ | +++ | ++ |
| Phe | ++ | ++ | ++ | +++ |  | +++ | +++ | ++ |
| Gly | ++ | +++ | ++ | + |  | +++ | +++ | ++ |
| His | ++ | ++ | ++ | +++ |  | +++ | +++ | ++ |
| Ile | ++ | ++ | ++ | +++ |  | +++ | +++ | ++ |
| Lys | ++ | ++ | ++ | +++ |  | +++ | +++ | ++ |
| Leu | ++ | ++ | ++ | +++ |  | +++ | +++ | ++ |
| Met | ++ | ++ | ++ | +++ |  | +++ | +++ | ++ |
| Asn | ++ | ++ | ++ | +++ |  | — | +++ | ++ |
| Pro | ++ | ++ | ++ | ++ |  | +++ | +++ | ++ |
| Gln | ++ | ++ | ++ | +++ |  | +++ | +++ | ++ |
| Arg | ++ | ++ | ++ | +++ |  | +++ | +++ | ++ |
| Ser | ++ | ++ | ++ | +++ |  | +++ | +++ | ++ |
| Thr | ++ | ++ | ++ | +++ |  | +++ | +++ | ++ |
| Val | ++ | ++ | ++ | +++ |  | + | +++ | + |
| Trp | ++ | ++ | ++ | +++ |  | +++ | +++ | + |
| Tyr | ++ | ++ | ++ | +++ |  | +++ | ++ | + |

-5-4-3-2-1 XXXXX Ser*/Thr* +1+2+3+4+5 XXXXX

FIG. 2A

| PEPTIDE | SEQUENCE | ANTIBODY DILUTIONS | | | | | | |
|---|---|---|---|---|---|---|---|---|
| | | 1.00E+03 | 5.00E+03 | 1.00E+04 | 5.00E+04 | 1.00E+05 | 5.00E+05 | 1.00E+06 |
| PXSP-P | X-X-X-X-Pro-X-Ser*-Thr*-Pro-X-X-X-X-Cys (SEQ ID NO:27) | 1.82 | 1.97 | 1.74 | 1.40 | 0.70 | 0.35 | 0.08 |
| Threonine mix | 18 phospho-Thr peptide mix | 1.97 | 1.37 | 0.67 | 0.36 | 0.13 | 0.07 | 0.05 |
| Ser/Thr | X-X-X-X-X-Ser/Thr-X-X-X-X-X-Cys (SEQ ID NO:28) | 0.14 | 0.03 | 0.01 | 0.00 | 0.00 | 0.00 | 0.00 |
| RB Thr373-P | Val-Ile-Pro-Pro-His-Thr*-Pro-Val-Arg-Thr-Val-Met-Asn-Thr-Cys (SEQ ID NO:30) | 2.07 | 2.17 | 1.70 | 1.20 | 0.48 | 0.18 | 0.03 |
| MKK3-Thr-P | Ser-Val-Ala-Lys-Thr*-Met-Asp-Gly-Ala-Gly-Cys (SEQ ID NO:31) | 0.06 | 0.04 | 0.01 | 0.00 | 0.00 | 0.00 | 0.00 |
| PKCalpha-P | Lys-Glu-His-Met-Met-Asp-Gly-Val-Thr-Thr-Arg-Thr*-Phe-Cys (SEQ ID NO:9) | 0.05 | 0.02 | 0.01 | 0.00 | 0.01 | 0.00 | 0.00 |
| p70 S6K-Thr389 | Asn-Gln-Val-Phe-Leu-Gly-Phe-Thr*-Tyr-Val-Ala-Pro-Lys-Lys-Cys (SEQ ID NO:8) | 0.11 | 0.05 | 0.01 | 0.00 | 0.01 | 0.00 | 0.00 |
| cdk4-Thr172-P | Arg-Ile-Tyr-Ser-Tyr-Gln-Met-Ala-Leu-Thr*-Pro-Val-Val-Lys-Cys (SEQ ID NO:32) | 2.07 | 2.21 | 2.01 | 1.55 | 0.69 | 0.31 | 0.07 |

FIG. 3A

| PEPTIDE | SEQUENCE | ANTIBODY DILUTIONS | | | | | |
|---|---|---|---|---|---|---|---|
| | | 1.00E+03 | 5.00E+03 | 1.00E+04 | 5.00E+04 | 1.00E+05 | 5.00E+05 |
| 14-3-3 BM-P | X-X-X-X-Arg-Ser-X-Ser*-X-Pro-X-X-X-X-Cys (SEQ ID NO:33) | 2.41 | 2.15 | 1.49 | 1.15 | 0.44 | 0.25 |
| 14-3-3 BM | X-X-X-X-Arg-Ser-X-Ser-X-Pro-X-X-X-X-Cys (SEQ ID NO:34) | 0.07 | 0.03 | 0.02 | 0.03 | 0.02 | 0.03 |
| CDC25-Ser216-P | Gly-Leu-Tyr-Arg-Ser-Pro-Ser*-Met-Pro-Glu-Asn-Leu-Asn-Arg-Cys (SEQ ID NO:35) | 2.35 | 2.08 | 1.49 | 1.05 | 0.33 | 0.18 |
| CDC25-Ser216 | Gly-Leu-Tyr-Arg-Ser-Pro-Ser-Met-Pro-Glu-Asn-Leu-Asn-Arg-Cys (SEQ ID NO:36) | 0.05 | 0.02 | 0.03 | 0.03 | 0.04 | 0.03 |
| Bad-Ser112-P | Thr-Arg-Ser-Arg-His-Ser-Ser*-Tyr-Pro-Ala-Gly-Thr-Glu-Glu-Cys (SEQ ID NO:37) | 1.59 | 0.43 | 0.10 | 0.03 | 0.01 | 0.00 |
| Bad-Ser112 | Thr-Arg-Ser-Arg-His-Ser-Ser-Tyr-Pro-Ala-Gly-Thr-Glu-Glu-Cys (SEQ ID NO:38) | 0.00 | 0.00 | 0.00 | 0.00 | 0.00 | 0.00 |
| Bad-Ser136 | Phe-Arg-Gly-Arg-Ser-Arg-Ser-Ala-Pro-Pro-Asn-Leu-Trp-Ala-Cys (SEQ ID NO:39) | 0.03 | 0.00 | 0.00 | 0.00 | 0.00 | 0.00 |
| Bad-Ser136-P | Phe-Arg-Gly-Arg-Ser-Arg-Ser*-Ala-Pro-Pro-Asn-Leu-Trp-Ala-Cys (SEQ ID NO:40) | 3.25 | 1.86 | 0.73 | 0.51 | 0.07 | 0.03 |

FIG. 4A

| PEPTIDE | SEQUENCE | MONOCLONAL ANTIBODIES | |
|---|---|---|---|
| | | 6B8 | 5A9 |
| Ser/ThrPro-P | X-X-X-X-X-X-Ser*/Thr-Pro-X-X-X-X-X-Cys (SEQ ID NO:26) | 1.774 | 0.731 |
| ProXSer/ThrPro-P | X-X-X-X-X-Pro-X-Ser*/Thr*-Pro-X-X-X-X-X-Cys (SEQ ID NO:27) | 0.924 | 0.766 |
| ProXSer/ThrPro-P | X-X-X-X-X-Pro-X-Ser/Thr-Pro-X-X-X-X-X-Cys (SEQ ID NO:41) | 0.02 | 0.063 |
| ProXSer/ThrProXArg-P | X-X-X-X-X-Pro-X-Ser*/Thr*-Pro-X-Arg/Lys-X-X-X-Cys (SEQ ID NO:42) | 1.955 | 1.275 |
| Thr-P | X-X-X-X-X-X-Thr*-X-X-X-X-X-X-Cys | 0 | -- |
| Ser-P | X-X-X-X-X-X-Ser*-X-X-X-X-X-X-Cys | 0.031 | 0.088 |
| Ser/Thr | X-X-X-X-X-X-Ser/Thr-X-X-X-X-X-X-Cys | 0.021 | 0.066 |
| Tyr-P | X-X-X-X-X-X-Tyr*-X-X-X-X-X-X-Cys | 0.023 | 0.072 |
| Rb (Ser795)-P | Ser-Pro-Tyr-Lys-Phe-Pro-Ser-Ser*-Pro-Leu-Arg-Ile-Pro-Gly-Cys (SEQ ID NO:43) | 0.032 | 0.124 |
| Rb (Thr373)-P | Val-Ile-Pro-Pro-His-Thr*-Pro-Val-Arg-Thr-Val-Met-Asn-Thr-Cys (SEQ ID NO:30) | 3.336 | 3.503 |
| Rb (Thr373) | Val-Ile-Pro-Pro-His-Thr-Pro-Val-Arg-Thr-Val-Met-Asn-Thr-Cys (SEQ ID NO:44) | 0.02 | 0.073 |

1 2 3 4

5 6 7 8

9 10 11 12

Signal to noise ratio of ELISA readings using phospho-Akt substrate antibody.

Western analysis of calyculin A-treated A431 cells using Phospho-Akt Substrate Antibody.

− +
calyculin A

Signal to noise ratio of ELISA reading using phospho-PKA substrates antibody.

Western analysis of calyculin A-treated A431 cells using Phospho-PKA Substrate Antibody.

- + calyculin A

Western analysis of A431 cell extracts

+ - + + - + - +  Cell Extracts
- - - + - - - -  PKI

Signal to noise ratio of ELISA reading using phospho-Serine/threonine phenylalanine antibody.

Western analysis of calyculin A-treated A431 cells using phospho-Serine/phenylalanine substrates antibody.

− + calyculin A

PRODUCTION OF MOTIF-SPECIFIC AND CONTEXT-INDEPENDENT ANTIBODIES USING PEPTIDE LIBRARIES AS ANTIGENS

This application is a continuation-in-part of, U.S. patent application Ser. No. 09/148,712, filed Sep. 4, 1998, now U.S. Pat. No. 6,441,140, the disclosure of which is hereby incorporated herein by reference.

BACKGROUND OF THE INVENTION

The present invention relates to the production of motif-specific, context-independent antibodies which are specific to at least one fixed amino acid residue in the context of variable surrounding amino acid or peptide sequences. Antibodies with these properties are useful in characterizing various forms of cellular regulation as well as serving to profile genome wide changes in cellular protein levels and protein modification.

Identifying the targets of intracellular signaling cascades are of major importance in understanding cell growth, differentiation, and cell death. Protein kinase cascades relay information from the cell surface to multiple cellular compartments including the nucleus and more distant cell processes such as synapses (Karin et al., Curr. Opin. Cell. Biol. 6:415–424 (1994)). Although a few targets of protein phosphorylation have been identified, most remain unknown, particularly those that regulate cell growth and differentiation For example, the MAP kinase cascade is known to play an important role in the regulation of cell growth (Lewis et al., Adv. Cancer Res. 74:49–139 (1998), Crowley et al., Cell 77:841–852 (1994)). However, beyond a handful of substrates, few protein targets responsible for the diverse actions of the MAP kinase cascade have been identified (Fukunaga and Hunter, EMBO 16(8):1921–1933 (1997), Stukenberg et al., Curr. Biol. 7:338–348 (1997)).

Another example of cell signaling proteins are the 14-3-3 proteins, which represent a phylogenetically conserved family of phosphoserine binding proteins whose precise role in cell signaling has yet to be determined (Burbelo and Hall, Curr. Biol. 5(2):95–96 (1995)). These proteins represent a large fraction of total brain protein and are known to bind a wide variety of signaling molecules including: ras, raf, bad, cdc25, and many others (Yaffe et al., Cell 91:961–971 (1997)). Recently, it has been shown that 14-3-3 proteins bind specifically to phosphorylated sites on proteins with the following motif: RXRSXS*XP where S* is phosphoserine and X represents any amino acid (Muslin et al., Cell 84:889–897 (1996), Yaffe et al. supra(1997)).

Similarly, histones have long been known to be modified by acetylation at specific lysine residues. Acetylation of lysine in histones is thought to reduce protein-DNA interactions and serve to open chromatin in regions undergoing transcription (Struhl, Genes & Development, 12:599–606 (1998)). Recently, other proteins associated with transcription complexes have been shown to be acetylated on lysine although the functional significance is unclear (Imhof et al., Curr. Biol. 7:689–692 (1997), Struhl supra (1998)).

Antibodies against phosphotyrosine have proven to be of great value in identifying and characterizing intracellular signaling mechanisms (Ross et al., Nature 294:654 (1981), Kozma et al., Method. Enzymol. 201:28 (1991), White and Backer, Method. Enzymol. 201:65 (1991), Kamps, Method. Enzymol. 201:101 (1991)). Their value derives from two properties; 1) their ability to discriminate whether or not a protein is tyrosine phosphorylated, and 2) their ability to react with a large variety of different proteins. These properties have proven invaluable in tracing intracellular signaling pathways and identifying new targets of activated tyrosine kinases.

Ideally, the most useful phosphotyrosine antibodies should be as general as possible, that is they should recognize phosphotyrosine independently of the protein sequences in which it is embedded (context independent) so as to allow detection of all possible phosphotyrosine residues. The most successful approaches for producing phosphotyrosine antibodies have utilized phosphotyrosine or phosphotyramine coupled via their free amino groups to keyhole limpet hemocyanin using hetero- or bifunctional crosslinking agents (Frackelton et al., Method. Enzymol. 201:79 (1991), White and Backer supra (1991), Wang, Method. Enzymol. 201:53 (1991), Kamps supra (1991)). Although currently produced polyclonal and monoclonal phosphotyrosine antibodies do recognize many different proteins, they often show crossreactivity with other phosphate containing compounds, for example, mononucleotides (Frackelton et al. supra (1991), Kamps supra (1991)). More importantly, most phosphotyrosine antibodies raised in this fashion display variable sequence reactivity, depending not only on the phosphorylated amino acid, but also upon the amino acid sequences surrounding phosphotyrosine. For example, the present inventors have observed that most phosphotyrosine antibodies do not recognize phosphotyrosine preceded by proline as found in the activation loop of JNK and hence do not react significantly with activated (tyrosine phosphorylated) JNK [(Tan et al. unpublished observations)]. The reason for the variable reactivity is likely due to the fact that the phosphotyrosine antigen is not presented directly to the immune system in the context of variable surrounding amino acids, but is instead presented as a hapten, inappropriately coupled to the KLH carrier via artificial linkages. This approach tends to produce antibodies that react well with phosphotyrosine but are sometimes blocked by surrounding amino acids as they are not present in the antigen.

Other approaches have utilized total cellular phosphotyrosine containing proteins as immunogens (Glenney, Method. Enzymol. 201:92 (1991), Wang supra (1991)) with considerable success but the context-dependence of the resulting antibody specificities was not carefully determined, although antibodies raised in this fashion did react with a majority of tyrosine phosphorylated proteins. Estimates as to the fraction of tyrosine phosphorylated proteins detected range from 50% to 94% (Kamps supra (1991)).

Attempts to use the above mentioned techniques to produce similar antibodies for phosphoserine and phosphothreonine have met with limited success. Antibodies produced to date have limited crossreactivity and lower affinity for phosphoserine or phosphothreonine probably due to the poor immunogenicity of these phospho-amino acids compared to phosphotyrosine (Heffetz et al., Method. Enzymol. 201:44 (1991)). Context-dependence and low affinity have limited the utility of currently available phosphoserine and phosphothreonine antibodies, especially when compared to phosphotyrosine antibodies Site-specific phosphoserine and phosphothreonine antibodies were first described by Nairn et al. in 1982 and have proven to be highly useful tools to study protein phosphorylation (Czernik et al., Method. Enzymol. 201:264 (1991), Czernik et al., Neuroprot. 6:56–61 (1995)). One drawback of this type of antibody is that a different antibody needs to be produced for each site of interest. Clearly, development of antibodies that detect phosphoserine or phosphothreonine in a context-independent fashion would be desirable for use in tracing serine/threonine kinase cascades and in defining their biological responses. Likewise, development of context-independent phosphotyrosine antibodies would overcome the limitations of currently available antibodies.

Motif-specific, context-independent antibodies would also be useful in identifying new targets of 14-3-3 action (i.e., other proteins phosphorylated at this motif) and in characterizing the protein kinases that phosphorylate these sites. Likewise antibodies reactive against acetylated lysine would serve as useful tools to study the functional significance of acetylation of histones.

Such antibodies can further be used as general reagents for detecting phosphorylation or other enzymatic modification in vitro, such as in high throughput kinase assays for drug screens, as a single antibody can be used to recognize many different phosphorylated substrates. Phosphotyrosine antibodies are currently employed in high throughput kinase assays to screen for selective, high affinity tyrosine kinase inhibitors. Compounds or drugs that block enzyme activity are detected by their ability to inhibit kinase activity as determined by a reduction of phosphotyrosine antibody binding to phosphorylated substrate. Similar assays can be set up to screen for pharmaceutically useful compounds using antibodies produced as described above for phosphoserine, phosphothreonine, or antibodies detecting other protein modifications.

Antibodies that detect short motifs in a context-independent fashion will also be particularly useful in profiling genome wide changes in protein levels and protein modification. For example, the use of context-independent phosphothreonine antibodies and 2D gel electrophoresis to profile genome wide changes in protein phosphorylation (Patterson and Garrels, *Cell Biology: A Laboratory Handbook* 249–257 (1994), Academic Press) as the result of drug treatment or overexpression of a particular protein will undoubtedly prove useful in identifying potential drug-protein interactions and suggest new downstream targets for overexpressed proteins.

SUMMARY OF THE INVENTION

In accordance with the present invention, there is provided a method of producing antibodies that selectively recognize specified short amino acid motifs independent of the surrounding amino acid, peptide, or protein sequences. The method allows the production of antibodies that recognize modified single amino acids, for example phosphorylated serine, threonine, and tyrosine, or acetylated lysine, as well other unmodified or modified motifs of one or more amino acids.

The method encompasses the production and purification of highly context-independent antibodies that recognize specific and highly degenerate amino acid motifs, such as those found in kinase consensus sequences or other enzyme binding sites. Furthermore, the method can be used to produce highly context-independent polyclonal or monoclonal antibodies.

Antibodies produced by the method of the present invention may be specific to virtually any protein motif, either modified or unmodified. For example, the method can be used to produce antibodies recognizing phosphothreonine alone or phosphothreonine in the context of several fixed amino acids as found in the MAPK, 14-3-3, or cdk consensus sites. It can also be used to produce antibodies specific for other modified amino acids, for example, acetylated lysine, or to detect any short motif of one or more amino acids, in a context-independent fashion.

The present invention further provides a method of profiling large and diverse protein populations on a genome-wide scale by utilizing motif-specific, context-independent antibodies against motifs conserved on such proteins. For example, phosphorylation-specific antibodies allow genome-wide profiling of changes in protein phosphorylation as a result of drug treatment.

The present invention also provides a method of identifying an unknown substrate of a known enzyme through the use of motif-specific, context-independent antibodies which are raised against motifs common to other substrates of the enzyme.

The use of such motif-specific, context-independent antibodies as a reagent for the detection of enzymatic modifications of a given motif within a substrate is also encompassed by the present invention.

BRIEF DESCRIPTION OF DRAWINGS

FIG. 1*a* is a table depicting the specificity of the affinity-purified, polyclonal antibodies produced against a phosphorylated threonine peptide library in Example I, when tested against specific peptides.

FIG. 1*b* is a table depicting the specificity of the phosphothreonine antibodies of Example I when tested against various phosphopeptide libraries.

FIG. 1*d* is a table depicting the context-independence of the anti-phosphothreonine antibodies of Example I as shown by immobilized grid.

FIG. 2*a* is a table depicting the specificity of the affinity-purified, polyclonal antibodies produced against a phosphorylated PXS*P peptide library in Example II.

FIG. 3*a* is a table depicting the lack of reactivity of the affinity-purified, polyclonal 14-3-3 antibodies of Example III when tested against non-phosphopeptides or phosphopeptides lacking the motif.

FIG. 4*a* is a table depicting the specificity of the monoclonal antibodies produced against a phosphorylated PXT*PXR library in Example IV.

DETAILED DESCRIPTION

Figure 1C:
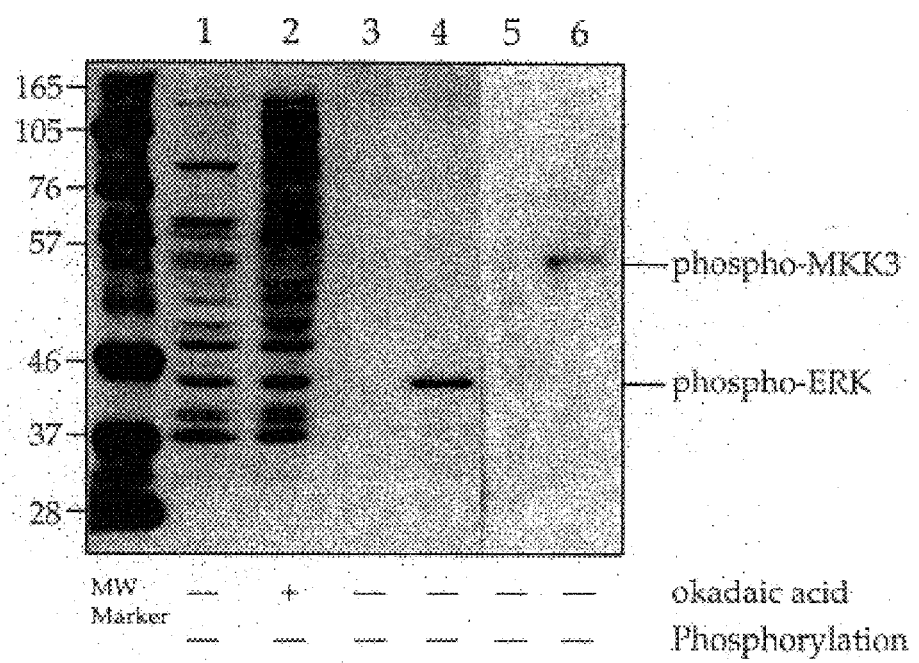
FIG. 1*c* is a Western analysis which depicts the reactivity of the phosphothreonine antibodies of Example I against cell extracts from cells treated with and without okadaic acid and against other phosphoproteins.

The present invention is based upon the concept that the concentration of any individual sequence in a peptide library used as antigen is extremely low and hence will be insufficient to drive an immune response in a host. The only antigenic determinants of sufficiently high concentration to drive the immune response are thus the fixed residues common to each sequence, as well as the peptide backbone itself.

Immunizing a host with peptide libraries representing all 20 amino acids at each degenerate position will produce antibodies tolerant to many, or all, amino acids at the variable positions surrounding one or more fixed residues. Such antibodies will then react with the antigenic determinant in the context of the broadest possible range of surrounding amino acid, peptide, or protein sequences. The fixed residue(s) of the motif may be a single unmodified or modified amino acid, such as a phosphorylated or unphosphorylated residue, or may be multiple unmodified or modified amino acids, such as a consensus recognition site.

As used herein, "antibodies" means polyclonal or monoclonal antibodies, including Fc fragments, Fab fragments, chimeric antibodies, or other antigen-specific antibody fragments.

As used herein, "motif-specific, context-independent antibodies" means antibodies which are specific against one or more fixed amino acid residues in the context of variable surrounding peptide or protein sequences; such antibody specificity is thus highly independent of the context in which the antigen occurs.

As used herein, "substrate" means any target molecule, including peptides or proteins, which an enzyme specifically recognizes and acts upon.

The general method by which motif-specific, context-independent antibodies are produced in accordance with the present invention is as follows:

(1) Motif-specific antibodies that react with any protein or -peptide containing specific target residues independently of the surrounding amino acids may be obtained by synthesizing a highly degenerate peptide library. In one preferred embodiment, the library comprises XXXXXXJ*XXXXXXC where X=all 20 amino acids except cysteine and J*=a modified (*) amino acid (J), for example, phosphothreonine (T*) or acetylated-lysine (K*). It will be appreciated that the specific target residue may be unmodified and that a shorter or longer library may be generated and less than all of the surrounding amino acids may be varied. In one preferred embodiment, the peptide library is about 6 to 14 residues long. While the preferred embodiment utilizes one fixed amino acid (either modified or unmodified) in a varied surrounding context, other preferred embodiments may utilize a motif comprising several fixed amino acids. Likewise, the surrounding sequence of the library may be varied at more than one position simultaneously, or, as in the preferred embodiment, varied at only one surrounding sequence position per degenerate molecule, such that a library is produced which is completely degenerate at every position except the fixed residue(s). The peptide library can be synthesized by standard F-Moc solid phase peptide synthesis using an ABI peptide synthesizer and using mixtures of each amino acid during degenerate coupling reactions.

The incorporation of modified amino acids at fixed positions should not be limited to phosphorylation or acetylations as other modified protected amino acids can also be incorporated, for example, amino acids modified with lipids (e.g. farnesylated, isoprenylated) or protected O-linked or N-linked sugars (e.g. glycosylated), methylated, or ribosylated amino acids, or nucleotides, polymers of nucleotides, nucleosides, or amino acids such as ubiquitin, or amino acid analogues.

The incorporation of unmodified amino acids at fixed positions may be selected to mimic conserved motifs, for example zinc fingers or repeating arginine residues.

(2) In order to produce as equal a representation of each amino acid as possible at each degenerate position, several rounds of altering the amino acid composition, synthesizing, and peptide sequencing are conducted. Amino acid sequence analysis at several different positions along the peptide is conducted to verify a random amino acid representation at each position and that the random representation is maintained throughout the synthesis. It will be recognized by one of skill in the art that the number of rounds may vary in order to achieve an equal distribution of all amino acids at each position.

(3) The highly diverse peptide library is used as an antigen, preferably by covalent coupling to a carrier. In a preferred embodiment, keyhole limpet hemocyanin (KLH) emulsified in Freund's adjuvant is used as the coupling agent, and the coupled peptide library injected intradermally into a host, such as female New Zealand white rabbits. Booster injections may be given in incomplete Freund's adjuvant until an immune response is obtained. Antibody titre is measured by a suitable method, such as ELISA against the motif-specific peptide libraries. Antisera raised in this manner may be used in both crude or purified preparations, as outlined below.

(4) Antisera from the most promising hosts are purified, for example over protein A, and adsorbed over a J (nonmodified) peptide library column. In the preferred embodiment, the nonadsorbed fraction (flow through) is then applied to a J* column, eluted at suitable pH, dialyzed and tested for J* specificity by a suitable method, such as ELISA using J* and J as antigen.

(5) Antibodies affinity purified in this fashion recognize the J* peptide library but do not react with the J library and exhibit a high degree of specificity for J*. These antibodies may be further tested for lack of reactivity against the unmodified form of the target modified amino acid, J*, or a J* homologue, utilizing a suitable method, such as ELISA.

(6) Antibodies may be further tested by western blotting, or another suitable method, using cell extracts prepared from cells treated with and without a selected protein modification enzyme inhibitor, such as protein phosphatase inhibitor okadaic acid. Treatments that increase protein modification will increase the number of antibody reactive proteins as well as the intensity of reactivity. The J* specific antibodies will react with a relatively small number of proteins from control extracts but will react with a very large number following treatment with the selected inhibitor. The antibodies will show no reactivity with the inactive-non-modified versions of these proteins, demonstrating a high degree of J* specificity and suggesting broad cross-reactivity to many different modified target containing proteins.

(7) The degree of context-independence may be more carefully examined, for example, by ELISA analysis against individual J* peptides that are mixed together or tested individually. Such analysis can indicate if poor reactivity occurs with certain motifs, such as when J* is followed by proline, for example.

(8) The context-dependence of J* antibody recognition may be further examined, as in the preferred embodiment, using a immobilized grid of modified-peptide libraries. In addition to a fixed target residue, J*, each different library is synthesized to contain an additional fixed amino acid at different positions relative to J* but with all other positions containing all 20 amino acids except cysteine. Each peptide library is coated, for example, on the bottom of an ELISA well and exposed to the J* antibodies. Antibodies that do not react with a particular spot (peptide library) on the grid do not bind when the specified amino acid is present at the specified position. This analysis determines whether or not a particular amino acid at a particular position relative to J* will allow or block binding.

Alternatively, purified antibodies can be linked to beads, allowed to bind the modified or unmodified library, unbound sequences washed away, and bound sequences recovered and subject to amino acid sequencing to determine the amount of each amino acid present at each position in the library. This information will indicate what amino acids are tolerated at each position.

(9) Monoclonal antibodies may be prepared, as in one form of the preferred embodiment, by coupling the J* peptide library to a suitable carrier, such as KLH, and injected into a host, such as BalbC mice. The J* peptide-KLH conjugate may be emulsified in Freund's adjuvant and booster injections in incomplete Freund's adjuvant may be carried out every other week until a response is obtained.

(10) Antibody titre is measured by a suitable method, such as ELISA against J* and non-J* peptide libraries. Sera from hosts showing high-titre responses are adsorbed with immobilized non-J* peptide and the nonadsorbed fraction tested by, for example, western blotting.

(11) Spleens from hosts showing J*-specific responses are fused to myeloma cells and hybridoma clones are selected and screened. Supernatants from individual clones are screened first for their ability to bind the J*-peptide library. Positive clones are next screened for their cross-reactivity against the non-J* library. Clones showing the highest degree of J*-specificity are chosen for further analysis as described above in steps (5) through (8).

(12) Overproduction of monoclonal antibodies resulting from step (11) above may be carried out, for example, by harvesting ascites, culturing selected hybridoma clones, or cloning into a host organism, such as E. coli.

The motif-specific, context-independent antibodies produced by this method may be used to identify an unknown substrate of an enzyme. Such antibodies are first generated against a motif that is recognized by the enzyme of interest, for example, a consensus site. These antibodies are then used to screen a sample for the presence of other, unknown substrates which contain the same motif. This method enables the rapid detection of important new substrates in a variety of cascades which involve conserved substrate motifs. For example, antibodies that selectively recognize a wide variety of proteins only when phosphorylated at the MAPK consensus phosphorylation site would greatly facilitate the detection of new MAP kinase targets. MAP kinase could be overexpressed in cell culture, activated by growth factors, and target substrate proteins identified by western blotting using antibodies that selectively recognize the phosphorylated substrate proteins (Stukenberg et al., Curr. Biol. 7:338–348 (1997). Alternatively, MAPK could be used to phosphorylate cDNA expression libraries in vitro and MAPK consensus-site antibodies used to identify cDNA clones expressing MAPK phosphorylated substrates (Funkunaga and Hunter, EMBO 16(8):1921–1933 (1997).

Similarly, antibodies produced by the method of the instant invention may be used to identify an enzyme which modifies a known substrate motif. Such antibodies, whether specific for modified (e.g. phosphorylated) or unmodified (e.g. zinc finger) motifs, can be used to detect whether a certain enzyme of interest has modified a substrate which contains that motif. This method allows for the rapid detection of important new proteins which act on known classes of substrates containing contain conserved motifs, for the example MAPK consensus site.

The motif-specific, context-independent antibodies of the instant invention may also be used in vitro as reagents in high-throughput assays, such as drug screens, to detect the enzymatic modification of certain substrates containing a conserved motif. For example, antibodies specific for a certain phosphorylated motif enable the rapid detection of inhibitors of the enzyme that act at that motif. In the case of a drug screen, a single motif-specific antibody can be used to assay the activity of a wide range of enzymes acting at many diverse sequence motifs. Phosphotyrosine antibodies are currently employed in high throughput kinase assays to screen for selective, high affinity tyrosine kinase inhibitors. Compounds or drugs that block enzyme activity are detected by their ability to inhibit kinase activity as determined by a reduction of phosphotyrosine antibody binding to phosphorylated substrate. Similar assays can be set up to screen for pharmaceutically useful compounds using antibodies produced as described above for phosphoserine, phosphothreonine, or antibodies detecting other protein modifications.

Antibody based detection of protein kinase activity has several advantages over radioactive assays for use in automated high throughput kinase assays. First, radioactive assays are difficult to automate because they employ transfer of 32-P gamma-labeled ATP to a peptide substrate. The phosphopeptide is then separated from labeled ATP using phosphocellulose filters and several washing steps, and finally, phosphorylation is quantitated by liquid scintillation methods. Together these steps are time consuming and difficult to automate. Antibody detection allows a wide variety of ELISA-type assays that are well suited for automation and high throughput screens.

Second, radioactive assays require low levels of ATP to insure high levels of 32-P incorporation for maximal sensitivity. Low levels of ATP in the kinase assay bias the search for inhibitors towards compounds that compete with ATP binding in the protein kinase catalytic cleft. Such screens consistently yield competitive inhibitors at the ATP binding site which due to the highly conserved nature of this binding site results in inhibitors with poor selectivity.

Current high-throughput kinase assays typically utilize biotinylated peptide substrates immobilized on the bottom of a 96 or 386 well plate that is subsequently incubated together with the desired protein kinase, ATP, and the appropriate kinase buffer. Kinase activity is measured using a fluorescently labeled phosphospecific-antibody that reacts only with the phosphorylated peptide substrate. These assays come in two formats homogeneous (not involving wash steps and heterogeneous (involving wash steps). Homogeneous fluorescent assays typically utilize lanthanide-labelled phosphoantibody binding to a phosphorylated peptide substrate that has linked to it an energy acceptor, for example allophycocyanin. Binding of the phosphoantibody the phosphorylated peptide substrate brings the two fluorophores close enough together to allow fluorescence resonance energy transfer to occur shifting the frequency of the emitted signal, indicating the presence of a biomolecular complex. Different compounds are added to each well and the ability of the compound to inhibit substrate phosphorylation is determined by inhibition of fluorescence energy transfer. This format is similar to the scintillation proximity assay commonly used in radioactive assays. Other homogeneous assays involve the use of fluorescence polarization to measure the binding of phosphoantibody to phosphorylated substrate.

The key feature in the homogeneous assays are the limited number of steps and the ease in automation. A large variety of heterogeneous kinase assays based upon ELIZA formats are also currently in use. These assays typically utilizing fluorescently labeled phosphoantibodies binding phosphorylated peptide substrates that are immobilized in 96 or 386 well formats. In this case wash steps are required to separate bound from unbound antibody. Fluorescently labeled antibody retained in the well is then detected using time resolved fluorescence.

The motifs used to generate antibodies for such modification screening assays may be either modified or unmodified substrate motifs. Antibodies generated against unmodified motifs will not bind if the substrate has been subsequently modified by an enzyme. Similarly, antibodies generated against modified motifs can detect increases in modified substrate concentrations owing to enzymatic activity.

Similar approaches may be applied to study a variety of other enzymatic modifications, and are not limited to the protein kinase or acetyltransferase activities discussed below. For example, the approach could be used to generate antibodies that recognize many other types of protein modification, including, but not limited to, the addition of sugars, methyl groups, carboxyl groups, the addition of various lipids, or the addition of nucleotides, or polymers of nucleotides, nucleosides, or amino acids such as ubiquitin.

Likewise, such motif-specific, context-independent antibodies may be used on a genome-wide scale to simultaneously profile large and diverse protein populations which contain conserved motifs. A specific two or three amino acid binding site, for example consecutive arginine residues, should appear (based upon a random distribution of amino acids) once every 400 or 8000 residues, respectively, (equating to approximately once per protein, or once every 20 proteins, respectively, (assuming the average protein is 400 amino acids)). Thus, an antibody specific for such a motif independent of the context in which it occurs allows for the rapid screening of a great number of proteins.

Phosphorylation specific antibodies allow genome wide profiling of changes in phosphorylation of proteins as a result of drug treatment or the overexpression of specific genes/proteins as a result of such treatment. Such antibodies also facilitate the profiling of expression of specific proteins in sequenced genomes.

For example, suppose that a drug is developed which inhibits the cell-cycle dependent protein kinase cdc2. The drug has been shown to inhibit cdk2 with high affinity, but the specificity of the compound needs to be further tested to examine whether other protein kinases are inhibited and if so, which ones.

As an early step in this process cell lines may be treated with the drug and the effects on total cell protein phosphorylation monitored using a panel of motif-specific and general phosphoantibodies to examine the nature of the phospho-substrates inhibited by the compound or lead drug.

Total protein from cell extracts prepared from control or drug treated cells may be fractionated using, for example, 2-dimentional gels (isoelectric focusing in the first dimension and standard SDS-polyacrylamide molecular weight fractionation in the second dimension), transferred to nitrocellulose membranes, and analyzed by western blotting using, in this hypothetical case, kinase consensus site-specific phosphoantibodies.

In this case, global analysis of total cell proteins using a cdc2 consensus site specific antibody would provide information regarding the ability of the drug to block phosphorylation at all potential cdc2 site substrates. The pattern of inhibition at other non-cdc2 substrates (i.e. the degree of specificity) could also be examined using antibodies to different kinase consensus sites, or using antibodies to phosphotyrosine to determine whether the inhibitor also acts to block tyrosine kinases.

Currently, for mammalian cells, the identity of the majority of protein "spots" visualized on 2-D gels are unknown. However, as all human genes are identified and sequenced and the corresponding proteins characterized and "spots" identified, analysis by protein profiling in accordance with the present invention will become even more powerfully informative. The identity of the proteins inhibited will not only confirm the drug specificity but the identity of additional "nonspecific" proteins inhibited will also suggest possible side effects. Identical analysis can be carried out in simpler, completely sequenced organisms, such as yeast where many of the protein "spots" on 2-D gels have already been identified.

The Examples presented below are only intended as specific preferred embodiments of the present invention and are not intended to limit the scope of the invention except as provided in the claims herein. The present invention encompasses modifications and variations of the methods taught herein which would be obvious to one of ordinary skill in the art.

The references cited above and below are herein incorporated by reference.

EXAMPLE 1

Context-independent Phosphothreonine Antibodies
Synthesis of peptide library antigens:

Phospho-specific antibodies that react with any protein containing phosphorylated threonine residues, i.e. that bind phosphothreonine independently of the surrounding amino acids, were obtained by synthesizing a highly degenerate peptide library XXXXXXThr*XXXXXXC where X=all 20 amino acids except cysteine and Thr*=phosphothreonine.

The phosphothreonine peptide library was synthesized by standard F-Moc solid phase peptide synthesis using an ABI peptide synthesizer and using mixtures of each amino acid during degenerate coupling reactions. Degenerate peptides were synthesized using an ABI model 433A peptide synthesizer, using FastMoc chemistry (Fields et al., *Pept. Res.* 4:95–101 (1991). hereby incorporated by reference herein) at a scale of 0.085 mmol. Fmoc/NMP chemistry utilizing HBTU amino acid activation (Dourtoglou et al., *Synthesis* 1984: 572–574 (1984), Knorr et al., *Tetra. Let.* 30:1927–1930 (1989), Knorr et al., in *Peptides* 1988 37–129 (1989), Walter de Gruter & Co, all hereby incorporated by reference herein) was employed for all cycles. Preloaded Fmoc-Cys(Trt) HMP (p-hydroxymethylphenoxymethyl) polystyrene resin functionalized at 0.5 mmol/g was used for each degenerate pool of peptides. Peptides were synthesized using single coupling during each cycle, although coupling times were extended at each position containing a phosphorylated amino acid. The final Fmoc was removed during synthesis. Utilization of preloaded HMP resin along with final Fmoc group removal yields peptides having both free amino and carboxy termini after cleavage and deprotection.

In order to produce as equal a representation of each amino acid as possible at each degenerate position several rounds of altering the amino acid composition, synthesizing, and peptide sequencing were conducted. The desired peptide pools were to contain an equimolar mix of 19 amino acids (all standard amino acids except Cys) at each "degenerate" site. Because the rate of reactivity of each protected amino acid differs, simply mixing equimolar amounts (each at approximately 5.26% of total) does not result in a population of peptides that is equimolar at each position. In order to maximize degeneracy at each residue, peptide synthesis was first done using equimolar "mixes" at each position. Phenylthiocarbamyl-amino acid analysis was performed therefore allowing assessment of relative amino acid content at each position. Based on amino acid analysis the molar amounts of each amino acid in the "mix" were adjusted to compensate for different reaction rates, in order to ensure equal representation of each amino acid at each degenerate position. Several rounds of peptide synthesis followed by amino acid analysis were necessary to optimize the amino acid mix, which resulted in a totally degenerate peptide.

The optimized amino acid mix arrived at was as follows: G (4.6%); A (5.6%); V (3.3%); L (2.5%); 1 (4.25%); S (4.4%); T (8.4%); F (2.25%); Y (6.0%); W (6.8%); M (2.9%); P (2.5%); D (5.8%); N (9.5%); E (6.2%); Q (9.4%); K (6.1%); R (6.4%); H (3.5%).

Cleavage of the degenerate peptides from the resin along with removal of side chain protecting groups occurs simultaneously upon treatment with TFA. The cleavage mixture (Perkin Elmer, Emeryville, Calif. (1995)) consists of the following: 0.75 g phenol, 0.125 ml methyl sulfide, 0.25 ml 1,2-ethanedithiol, 0.5 ml milliQ H2O, 0.5 ml thioanisol, 10 ml TFA. The entire mixture was added to the peptide resin (approx. 300 mg). The resin was flushed with nitrogen and gently stirred at room temperature for 3 hours. The resin was then filtered allowing the peptide to be precipitated into cold (0° C.) methyl-t-butyl ether. The ether fraction was centrifuged allowing collection of the precipitate. The peptide precipitate was vacuum dried, analyzed by mass spectroscopy, and HPLC purified.

A sample of the peptide was dissolved in acetonitrile/water (50:50, v/v) and analyzed on a Perceptive Biosystems (Framingham, Mass.) MALDI-TOF mass spectrometer using 2,4,6-trihydroxyacetophenone plus ammonium citrate as the matrix. As expected, the peptide mixture did not show a homogeneous product. MALDI-TOF analysis demonstrated that the peptide pool was degenerate, showing an average mass and the expected statistically normal curve of peptide mass.

Peptides were purified using a Waters HPLC system consisting of a Lambda-Max Model 481 Multiwavelength detector, 500 series pumps, and Automated gradient controller. A Vydac semi-preparative C18 column was used for reverse-phase purification. A 60 min. linear gradient, 10%-100% B, was used at a flow rate of 2 ml/minute. Buffer A consisted of 0.1% TFA/H$_2$O (v/v) while buffer B consisted of 0.1% TFA/60% CH$_3$CN/40% H$_2$O (v/v/v). Detection was at 214 nm.

Because the peptide pool was degenerate (as demonstrated by mass spectroscopy) HPLC purification was not expected to yield a homogeneous product. Base-line separation of peptide mixtures was not achieved by this method and it was only intended as a crude purification/desalting step. Mass spectroscopy was performed and all fractions whose mass was within the theoretical range were pooled and lyophilized Amino acid sequence analysis at several different positions along the peptide indicated a random amino acid representation at each position and that the random representation was maintained throughout the synthesis. The results indicated the production of highly diverse peptide libraries that would serve as suitable antigens.

Production of Rabbit polyclonal antibodies:

All peptides synthesized contained C-terminal cysteine residues allowing conjugation to the carrier protein (KLH) using the heterobifunctional cross-linking reagent m-maleimidobenzoyl-N-hydroxysuccinimide ester (MBS). The conjugation procedure used was as described by the manufacturer (Pierce), although the amount of peptide coupled to KLH was increased to 10 mg in order to provide increased material for immunization and boosting of animals. Scale-up required use of a larger desalting column (Bio-Rad 10 DG (Cambridge, Mass.)) to remove the excess MBS after reaction to N-termini and the e-amino group of KLH Lysine residues.

The phosphothreonine peptide library was covalently coupled to keyhole limpet hemocyanin (KLH) (250 μgrams), emulsified in Freund's adjuvant and injected intradermally into female New Zealand white rabbits. Booster injections (200 μgrams) in incomplete Freund's adjuvant were carried out every other week until a response was obtained. Rabbit sera was screened at three week intervals for the presence of phosphopeptide specific immunoreactivity by ELISA using both the phosphothreonine and non-phosphothreonine peptide libraries. When the titre of antibody against phosphopeptide reached $10^5$, rabbits were put on a production bleed schedule with bleeds collected every two weeks. When 40 ml of high titre serum were obtained, purification of phosphospecific antibodies was initiated, as described below.

Antisera from the most promising rabbit was purified over protein A and passed over a nonphospho Thr/Ser peptide library column. The nonadsorbed fraction (flow through)

was applied to a phosphothreonine column, eluted at low pH, dialyzed and tested for phosphospecificity by ELISA using phospho- and nonphosphopeptides. Antibodies affinity-purified in this fashion recognized the phosphorylated threonine peptide library but did not react with the nonphosphothreonine/serine library, indicating a high degree of specificity for phosphothreonine (see FIG. 1a). ELISA results also indicated that the antibodies also reacted specifically with a mixture of 18 different phosphothreonine peptides but showed no reactivity with any of the corresponding nonphosphopeptides (FIG. 1b). The antibodies also exhibited a strict preference for phosphothreonine, showing no reactivity with a mixture of 38 different phosphoserine peptides (FIG. 1b) or peptides containing phosphotyrosine.

We next tested the antibodies by western blotting using cell extracts prepared from cells treated with and without the protein phosphatase inhibitor okadaic acid. As shown in FIG. 1c the phosphothreonine antibodies react with a relatively small number of proteins from control extracts but react with a very large number following treatment with okadaic acid (see the smear of high Mol Wt. reactive proteins in FIG. 1c, lane 2). The antibodies also reacted specifically with the active forms of MAPK (ERK1) and MKK3 only when phosphorylated at threonine residues in their respective activation loops. The antibodies showed no reactivity with the inactive-nonphosphorylated versions of these proteins (FIG. 1c, lanes 3–6). These results demonstrate a high degree of phosphothreonine specificity and suggest broad cross-reactivity to many different threonine-phosphorylated proteins and peptides.

Figure 2B:
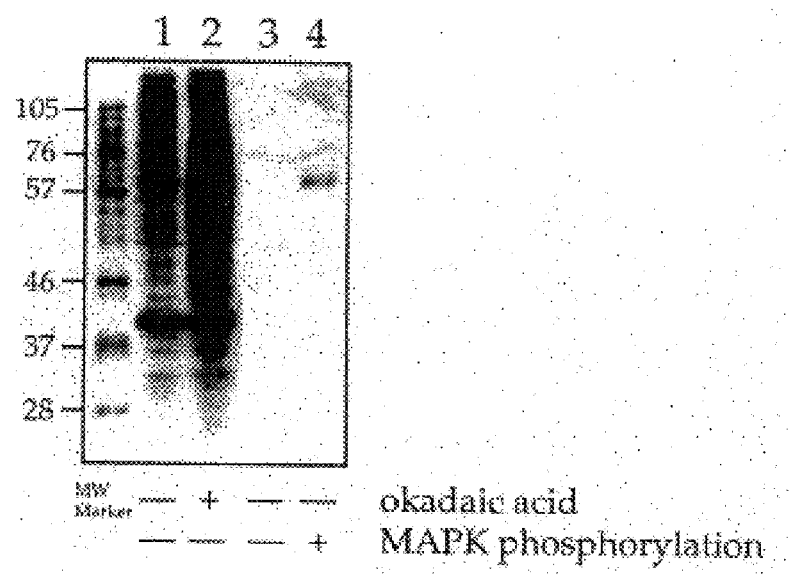
FIG. 2*b* is a Western analysis depicting the reactivity of the phospho-PXS*P antibodies of Example II against cell extracts from cells treated with and without okadaic acid and against other phosphoproteins.

To examine more carefully the degree of context-independence, ELISA analysis was conducted against individual threonine phosphorylated peptides that were mixed together in the previous experiment. As shown in FIG. 1a, the phosphothreonine antibody reacts well with all phosphopeptides except those where phosphothreonine is immediately followed by proline, for example the c-Myc and APP1 phosphopeptides (FIG. 2b). These results indicate that purified rabbit antibodies reacted in a phosphospecific manner with a wide variety of phosphothreonine but react only poorly with phosphopeptides where the phosphorylated threonine is followed by proline.

The context-dependence of phosphothreonine antibody recognition was further examined using a immobilized grid of phosphopeptide libraries. In addition to a fixed phosphothreonine, each different library was synthesized to contain an additional fixed amino acid at the −4, −3, −2, −1, +1, +2, +3 positions relative to phosphothreonine but with all other positions containing all 20 amino acids except cysteine. Each peptide library was coated on the bottom of an ELISA well and exposed to the phosphothreonine antibodies. Antibodies that do not react with a particular spot (peptide library) on the grid do not bind when the specified amino acid is present at the specified position. This analysis determines whether or not a particular amino acid at a particular position relative to phosphothreonine will allow or block binding (FIG. 1d).

Results confirmed that the phosphothreonine antibodies tolerate all amino acids in the −1, −2, −3, −4, and +2, +3 position, and bound equally well to every amino acid except proline at the +1 position (see FIG. 1d, first row). The reactivity as defined by this binding profile indicates that the antibodies will bind all phosphothreonine containing sequences except those followed immediately in +1 position by proline. Further analysis using a variety of specific phosphothreonine containing peptides confirmed these results.

Phosphothreonine specific antibodies from several other rabbits immunized with the same peptide library antigens were further purified and characterized. Antibodies purified from sera obtained from two other rabbits also produced broadly cross-reacting phosphothreonine antibodies as determined by ELISA. One rabbit produced antibodies that react equally well with peptides containing proline following the phosphothreonine.

Taken together, these results demonstrate the broad context-independence of the phosphothreonine response obtained when combinatorial peptide libraries are used as immunogens.

EXAMPLE II

Protein Kinase Consensus Site-Specific Phosphoantibodies

MAPK-consensus recognition sites: PXS*P

A peptide library of the preferred site for MAPK phosphorylation PXS*P was synthesized (FIG. 2a) substantially as described in Example I. In addition to an equimolar mix of phosphoserine and threonine, amino acids at two other positions were also fixed; proline at −2 and proline at +1. This library was coupled to KLH and injected into rabbits as described for phosphothreonine. IgG from the most promising rabbit was protein A purified and passed over a nonphospho-Thr/Ser peptide library column. The nonadsorbed fraction (flow through) was applied to a phospho-PXS*P column, eluted at low pH, dialyzed and tested for phosphospecificity by ELISA using phospho- and nonphosphopeptides.

Antibodies affinity purified in this fashion reacted strongly with the phosphorylated PXS*P peptide library but did not react with the nonphosphothreonine/serine library (see FIG. 2a). ELISA results also indicated that the antibodies also reacted specifically with a mixture of 18 different phosphothreonine peptides but showed no reactivity with any of the corresponding nonphosphopeptides (FIG. 2a). In addition to being phosphospecific, the antibodies exhibited a preference for proline at the −2 and +1 positions and showed no reactivity with phosphorylated peptides that lack proline at this position (FIG. 2a). The antibodies reacted strongly with the RB and cdk4 phosphopeptides but showed no reactivity with the MKK3, PKCalpha, or p70S6 phosphopeptides that lack proline at the +1 position (FIG. 2a). These antibodies do react with some peptides lacking proline at −2, for example the cdk4 phosphopeptide, suggesting that proline at this position is not absolutely necessary.

PXS*P antibodies were further tested by western blotting using cell extracts prepared from cells treated with and without the protein phosphatase inhibitor okadaic acid. Binding of the PXS*P antibodies to cell extracts from RS 4;11 cells was strongly enhanced following treatment with okadaic acid (smear of high Mol Wt. proteins in FIG. 2b, lane 2). The antibodies also reacted specifically with ATF-2.phosphorylated in vitro with MAP kinase but not the nonphosphorylated form of this protein (FIG. 2b, lanes 3 and 4), demonstrating a high degree of phospho-specificity and broad cross-reactivity to many different phosphorylated proteins and peptides.

The specificity of PXS*P antibody recognition was also examined using an immobilized grid of phosphopeptide libraries. As described above, in addition to a fixed phosphothreonine or phosphoserine, each different library was synthesized to contain an additional fixed amino acid at the −1, +1, +2 positions relative to phosphothreonine but with all other positions containing all 20 amino acids except cysteine.

The PXS*P antibody reacted weakly with peptide libraries where proline was fixed at the −1 position and reacted strongly with libraries where proline was fixed at both the −2 and +1 positions. The reactivity as defined by this binding profile indicates that the PXS*P antibodies strongly bind only sequences containing the PXS*P motif, as expected, but that the antisera still contain some residual reactivity to S*P (as a result of impurities), which could be removed by further purification using immobilized S*P peptide library.

EXAMPLE III

Protein Kinase Consensus Site-Specific Phosphoantibodies 14-3-3 binding site: RSXS*XP Antibodies that identify 14-3-3 targets were obtained by synthesizing a peptide library: XRSXS*XPXC where S* is phosphoserine and X represents any amino acid and C is cysteine. The above 14-3-3 phosphopeptide library was synthesized by standard F-Moc solid phase peptide synthesis using an ABI peptide synthesizer and mixtures of each amino a acid except cysteine during degenerate coupling reactions, as discussed in Example I.

Figure 3B:
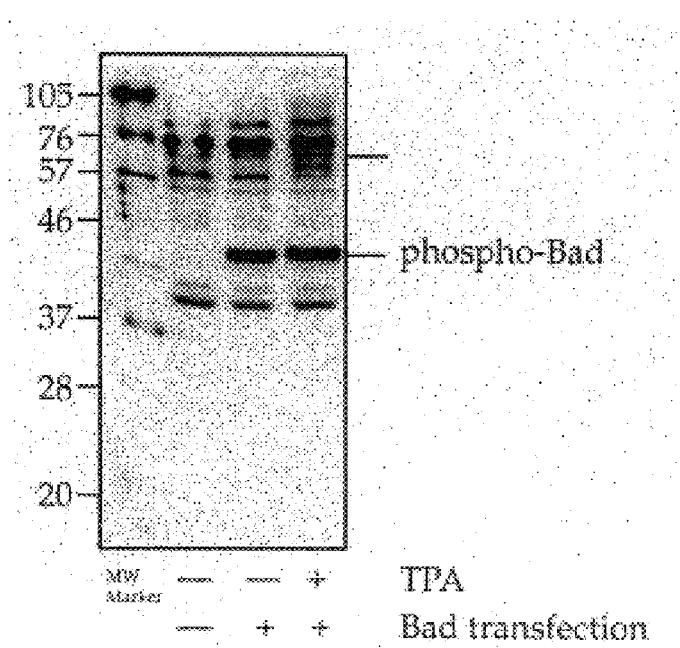
FIG. 3*b* is a Western analysis depicting the reactivity of the phospho-14-3-3 antibodies of Example III against cell extracts from cells transfected with GST-Bad and with TPA.

The 14-3-3 phosphopeptide library was coupled to KLH and injected into rabbits as described above for phosphothreonine and PXS*P. Antisera from the most promising rabbit was purified over protein A and adsorbed over a nonphospho-14-3-3 peptide library column. The flow-through of this column was applied to a phospho-14-3-3 column eluted at low pH, dialyzed and tested for phospho-specificity by ELISA using phospho-and nonphospho-14-3-3 peptide libraries. These affinity purified phospho-14-3-3 antibodies recognized the phosphorylated 14-3-3 peptide library but not the nonphospho-14-3-3 library, indicating a high degree of specificity for phospho-14-3-3 (see FIG. 3a). The antibodies also reacted strongly with several different peptides containing the 14-3-3 motif including; phospho-Bad-Ser136, cdc25-Ser216, and more weakly with phospho-Bad-Ser112 which contains a slight variant motif. The antibodies showed no reactivity with the corresponding nonphospho-peptides (FIG. 3a) or with many other phosphopeptides that did not contain the motif.

Phospho-14-3-3 antibodies were further tested by western blotting using cell extracts prepared from cells transfected with a GST-Bad fusion protein and treated with and without the phorbol ester TPA. The antibodies reacted with a small number of proteins from control extracts (see FIG. 3b). Bad was detected in extracts prepared from transfected cells but not control cells. Since the basal level of Bad phosphorylation is high it was difficult to see increased phosphorylation with TPA, although TPA did induce the phosphorylation of several higher molecular weight proteins (arrow in FIG. 3b). These results indicate that the phospho-14-3-3 antibodies can detect phosphorylated Bad and other TPA stimulated phospho-proteins.

ELISA analysis against the previously described grid of serine/threonine phosphorylated peptide libraries was also conducted. As expected, the phospho-14-3-3 antibodies have an absolute requirement for proline at the +2 position.

EXAMPLE IV

Production of Mouse Monoclonal Antibodies: CDK Consensus Phosphorylation Site PXT*PXR The PXT*/S*PXR sequence represents a consensus phosphorylation site for many of the cell cycle-dependent proteins kinases (cdks). Antibodies that recognize this phosphorylated motif would be useful to identify new cdk substrates important in controlling cell cycle progression. The PXT*/S*PXR peptide library shown in FIG. 4a was coupled to KLH and injected into Balb/c mice. The phosphopeptide-KLH conjugate (50 μgrams) emulsified in Freund's adjuvant was injected IP. Booster injections (12.5 to 25 μgrams) in incomplete Freund's adjuvant were carried out every three weeks until a response was obtained. Antibody titre was measured by ELISA against the immunized phosphopeptide library. Sera from mice showing high-titre responses were adsorbed with immobilized nonphospho Thr/Ser peptide and the nonadsorbed fraction tested by western blotting (data not shown).

Splenocytes from a mouse showing phosphospecific responses were fused to myeloma X63Ag8.635 cells (Kearney et al., *J. Immunol.* 123:1548–1550 (1979)) and approximately 1,100 hybridoma clones were selected and screened. Supernatants from individual clones were screened first for their ability to bind the immunized phosphopeptide library and next for their cross-reactivity against the non-phosphopeptide library. Two different clones showing the highest degree of phospho-specificity were chosen for further analysis. The specificity of clones 6B8 and 5A9 were further characterized using the phosphopeptide libraries and phosphopeptides shown in FIG. 4a. Both clones reacted specifically with phosphothreonine containing libraries and individual peptides but did not significantly react with phosphoserine containing peptides, indicating that phosphothreonine selective clones had been identified. Both clones reacted strongly with peptide libraries where proline is fixed in the −2 and +1 positions relative to phosphothreonine. Reactivity against T*P and PXT*P libraries does not indicate relaxed specificity since one of 400 and one of peptides in the respective libraries will have the appropriate amino acids at the fixed positions. Both clones reacted strongly with a single RB phosphothreonine peptide containing each of the fixed positions present in the immunized library but did not react significantly with the corresponding nonphosphopeptide.

Figure 4B:
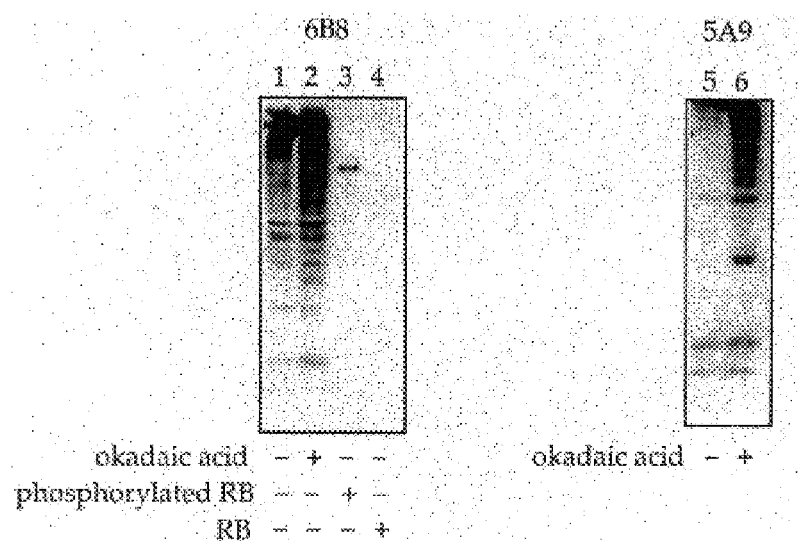
FIG. 4*b* is a Western analysis depicting the reactivity of the CDK consensus site monoclonal antibodies of Example IV against phosphorylated and nonphosphorylated RB protein.

Western analysis shows that okadaic acid treatment of cultured cells dramatically increases the reactivity with both clones 6B8 and 5A9 (FIG. 4b). Clone 6B8 is also shown to detect cdc2 phosphorylated RB by western blotting (FIG. 4b) but does not react with nonphosphorylated RB protein. Clone 5A9 was deposited in accordance with the terms and conditions of the Budapest Treaty on Sep. 4, 1998 with the American Type Culture Collection under ATCC Accession No. HB1 2563.

EXAMPLE V

Acetylated Lysine Specific Antibodies

Antibodies specifically reactive against acetylated lysine but not reactive against non-acetylated lysine were obtained by synthesizing the following acetylated lysine peptide library: XXXXXXK*XXXXXXC where K* is acetylated and X represents any amino acid except cysteine and C is cysteine. The acetylated lysine peptide library was synthesized as described previously by standard F-Moc solid phase peptide synthesis using commercially available fully protected acetylated lysine.

The peptide library was coupled to KLH and injected into rabbits. The K*-peptide-KLH conjugate (250 μgrams) was used as immunogen as described for the other phosphopeptide libraries. Antisera from the most promising rabbit were purified over protein A and adsorbed over a non-acetylated lysine peptide library column. The flow through of this column was applied to an acetylated lysine column, eluted at low pH, dialyzed and tested for phosphospecificity by ELISA.

Figure 5A:
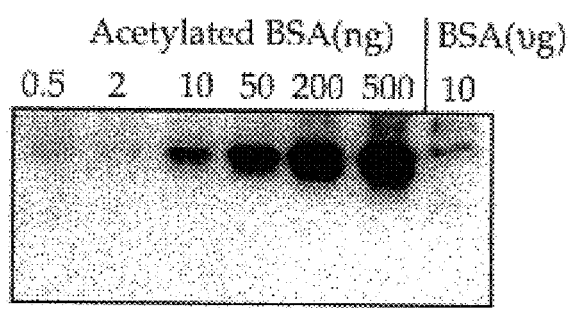
FIG. 5*a* is a Western analysis depicting the specificity of the acetylated-lysine antibodies of Example V against acetylated BSA.

Acetylated-lysine antibodies, affinity purified as described above, recognized the acetylated lysine peptide library but not the non-acetylated library, indicating a high degree of specificity for acetylated lysine as measured by ELISA. The antibodies also reacted specifically with as little as 0.5 ng of acetylated bovine serum albumin (BSA) but showed no reactivity with up to 10 μgrams of nonacetylated BSA (see FIG. 5a).

Figure 5B:
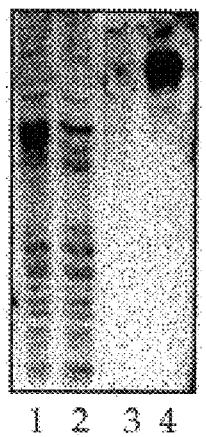
FIG. 5*b* is a Western analysis depicting the reactivity of the acetylated-lysine antibodies of Example V against various proteins present in C6-cell extracts when antibodies are preincubated with nonacetylated peptide library.
Figure 5C:
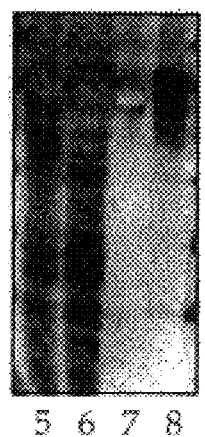
FIG. 5*c* is a Western analysis depicting the reactivity of the acetylated-lysine antibodies of Example V against various proteins present in C6-cell extracts when antibodies are preincubated with acetylated peptide library.
Figure 5D:
FIG. 5d is a Western analysis depicting the reactivity of the acetylated-lysine antibodies of Example V against the control acetylated BSA when antibodies are preincubated with acetylated peptide library.

The antibodies were further examined by western blotting using cell extracts prepared from cells treated with and without anisomycin. The antibodies react with a number of different proteins present in the C6-cell extracts (FIG. 5b). In panels b and c, antibodies were preincubated with 1 μgram of nonacetylated peptide library (FIG. 5b) or 1 μgram of acetylated peptide library (FIG. 5c). Preincubation with nonacetylated peptide library had little effect on antibody reactivity with acetylated control protein or bands visualized in the cell extract (FIG. 5c, lanes 5–8). However, preincubation of the antibodies with the acetylated lysine peptide library completely blocked antibody binding to control acetylated BSA as well as binding to many proteins present in the cell extract (FIG. 5d, lanes 9–12). These results demonstrate a high degree of specificity for acetylated lysine and indicate that the antibodies recognize a broad spectrum of different sized proteins that contain acetylated lysine in a variety of surrounding sequence contexts (compare FIG. 5c and d, lanes 1, 2).

EXAMPLE VI

Phosphoantibody to the Substrate Consensus Sequence for Akt: RXRXXT*

The Akt protein kinase is an important regulator of cell survival and insulin signaling, but very few of its in vivo targets have been identified. Studies with synthetic peptide substrates of Akt (D. R. Alessi et al. FEBS Lett. 399:333–338 (1996)) as well as the analysis of known Akt phosphorylation sites on GSK-3 (T.F. Franke et al. Cell 88:435–437 (1997)), Bad (M. Pap et al. J. Biol. Chem. 273:19929–19932 (1998); Datta et al. Cell 91:231–241 (1997)), FKHR Brunet et al. Cell 96:857–868 (1999)), and Caspase-9 (M. H. Cardone et al. Science 282:1318–1321 (1998)) indicate that Akt phosphorylates its substrates only at a serine or threonine in a conserved motif characterized by arginine at positions −5 and −3.

To study and discover new Akt targets, an antibody was developed that specifically recognizes the phosphorylated form of the Akt substrate consensus sequence RXRXXT*. This antibody was raised against the following synthetic peptide antigen, where X represents a position in the peptide synthesis where a mixture of all twenty amino acids were used, and Thr* represents phosphothreonine: Cys-X-X-X-Arg-X-Arg-X-X-Thr*-X-X-X-X (SEQ ID NO: 45). The synthetic phospho-peptide was conjugated to KLH (keyhole limpet hemocyanin) and injected into rabbits. Test bleeds were collected and characterized by ELISA on phospho and non-phospho versions of the peptide antigen.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia AKTA FPLC to isolate the IgG antibody fraction. Affinity chromatography is then performed using peptide coupled to SulfoLink resin from Pierce (#20401; coupling directions according to manufacturer). Phospho-Akt Substrate Antibody was found to be already highly phosphospecific as crude serum, so that a subtraction step on a column containing the non-phospho peptide was not necessary and the elution from the Protein A column could be used directly for affinity chromatography on a phospho-peptide-containing column. Protein A eluate was incubated with phospho-peptide resin by rotation in a sealed column at room temperature for one hour. Column was then drained, washed twice with PBS, and eluted with 0.1M Glycine, pH 2.7 and pooled fractions neutralized with 1M Tris-HCl, pH 9.5 (-1-2% of fraction volume). The eluted phosphospecific antibody was then dialyzed overnight in PBS at 49C.

Figure 6:
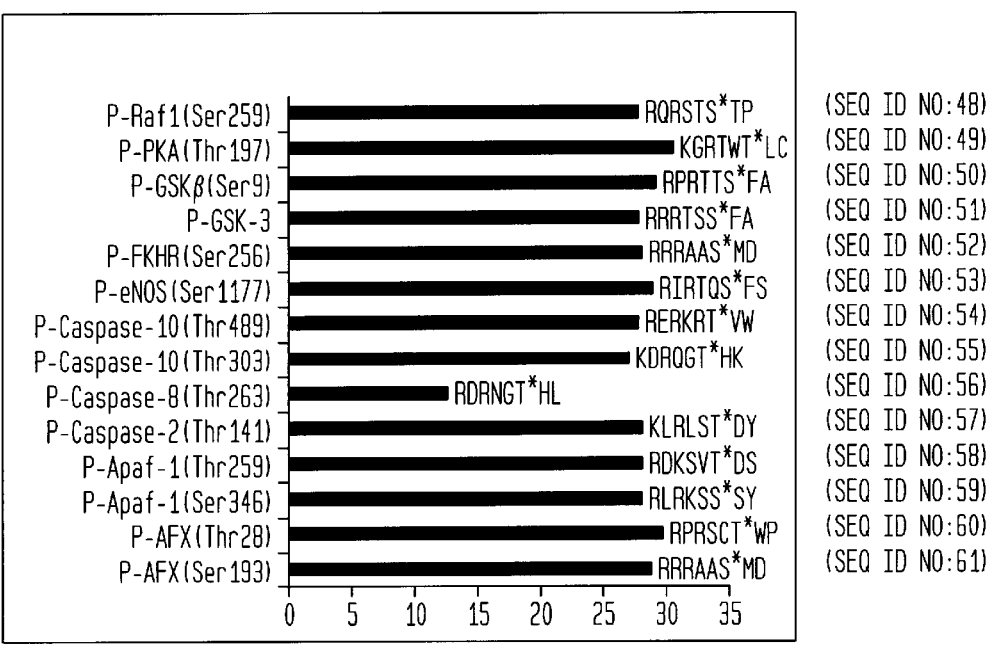
FIG. 6 shows the signal to noise ratio of ELISA readings using phospho-Akt substrate antibody with phospho-peptides of Akt substrates vs. non-phospho-peptides of Akt substrates.
Figure 7:
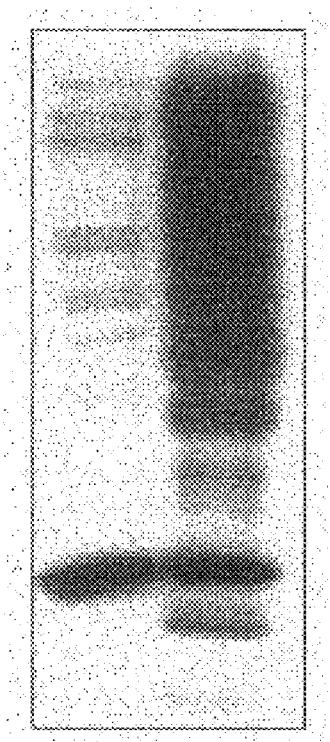
FIG. 7 is a Western analysis of calyculin A-treated A431 cells using phospho-Akt substrate antibody.

The resulting antibody is highly specific for peptides which contain phospho-threonine/serine preceded by arginine at positions −5 and −3 (FIG. 6) Some cross-reactivity is observed for peptides which contain arginine at positions −3 and −2. (FIG. 6) also shows that this antibody is highly phospho-specific and recognizes these motifs only when phosphorylated (signal to noise ratios were determined as a ratio of reactivity with the phosphopeptide to reactivity with the corresponding non-phosphopeptide). This antibody does not recognize other phosphothreonine/serine containing motifs. (FIG. 7) indicates that in mammalian cells there are many phosphoproteins recognized by this antibody.

EXAMPLE VII

Phosphoantibody to the Substrate Consensus Sequence for PKA: RRXT* cAMP-dependent Protein Kinase A (PKA) is an important kinase for regulating a striking number of physiologic processes, including intermediary metabolism, cellular proliferation and neuronal signaling, by altering basic patterns of gene expression (M. Montminy Annual Rev. Biochem. 66:807–822 (1997)). Studies with synthetic peptide substrates have established a consensus phosphorylation site for PKA, namely serine or threonine with arginine at the −2 and −3 positions (Z. Songyang et al. Current Biology 4:973–982 (1994)).

To identify and study new in vivo substrates of PKA, an antibody was developed that specifically recognizes the phosphorylated form of the PKA substrate consensus sequence RRXT*. The following synthetic phospho-peptide peptide antigen was used, where X represents a position in the peptide synthesis where a mixture of all twenty amino acids were used, and Thr* represents phosphothreonine: Cys-X-X-X-X-X-Arg-Arg-X-Thr*-X-X-X-X (SEQ ID NO: 46). The synthetic phospho peptide was conjugated to KLH (keyhole limpet hemocyanin) and injected into rabbits. Test bleeds were collected and characterized by ELISA on phospho and non-phospho versions of the peptide antigen.

Once rabbits started to show high phospho-specific titers, 40 ml production bleeds were obtained. Bleeds were dialyzed overnight in 0.025M NaAcetate, 0.01M NaCl pH=5.2 at 4° C., then spun at 11,200 rpm at 4° C. for 30 min to precipitate serum lipids. Serum supernatant was then purified by Protein A chromatography on a Pharmacia (Piscataway, N.J.) AKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Protein A eluate was first incubated with non-phospho-peptide resin by rotation in a sealed column at room temperature for one hour, in order to remove antibodies reactive with the non-phospho version of the protein antigen. This resin was then drained and the flow-through then incubated with phospho-peptide resin. This column was drained, washed twice with PBS, phospho-specific antibody eluted with 0.1M Glycine, pH 2.7 and pooled fractions neutralized with 1M Tris-HCl, pH 9.5 (~1–2% of fraction volume). The eluted phosphospecific antibody was then dialyzed overnight in PBS at 4° C.

Figure 8:
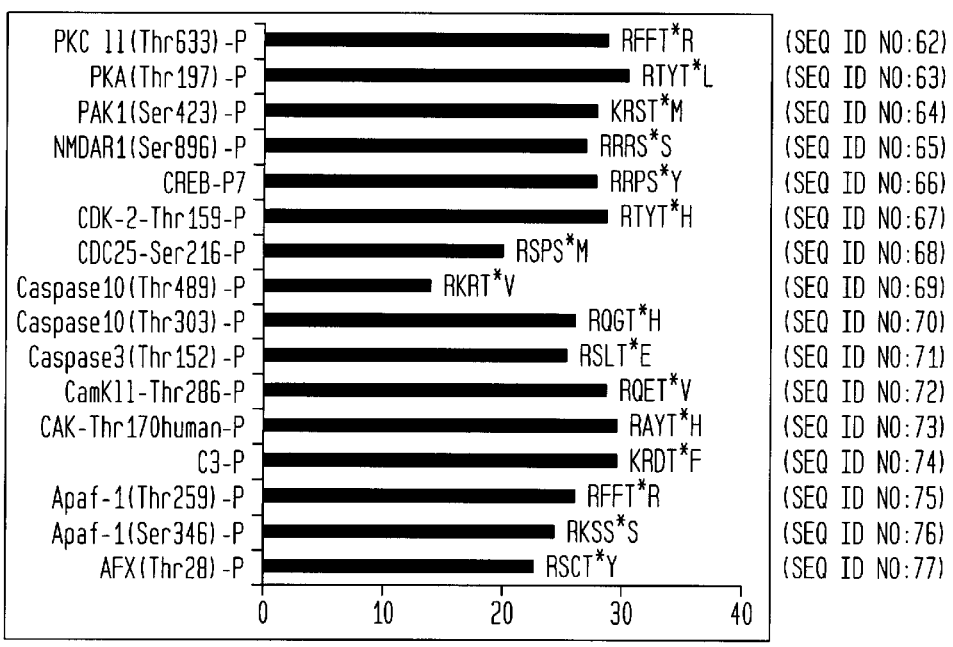
FIG. 8 shows the signal to noise ratio of ELISA reading using phospho-PKA substrates antibody against peptides have arginine or lysine at −3 position.
Figure 9:
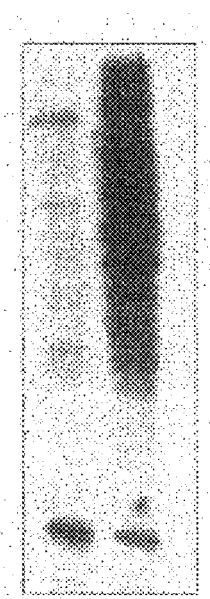
FIG. 9 is a Western analysis of calyculin A-treated A431 cells using phospho-PKA substrates antibody.
Figure 10:
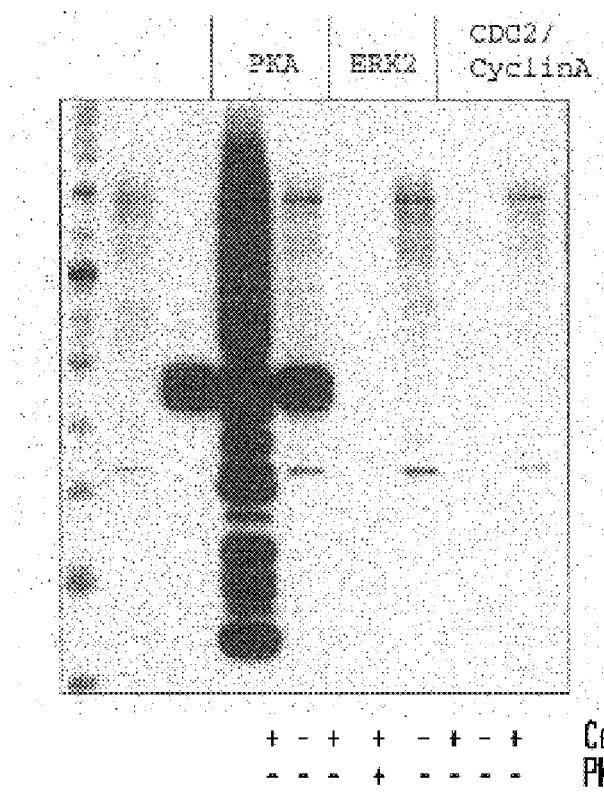
FIG. 10 is a Western analysis of A431 cell extracts phosphorylated by protein kinase A, ERK2 and CDC2/cyclinA in vitro using phospho-PKA substrate antibody.

FIG. 8 shows that the resulting antibody is highly specific for peptides or proteins containing phospho-threonine with arginine at the −3 position. The antibody also recognizes some proteins containing phospho-serine with arginine at the −2 and −3 position. It does not recognize the non-phosphorylated version of these motifs (as shown by the signal to noise ratios in FIG. 8 which were determined as a ratio of reactivity with the phospho-peptide to reactivity with the corresponding non-phospho-peptide); nor does the antibody recognize other phosphoserine/threonine containing motifs. FIG. 9 indicates that in mammalian cells there are many phosphoproteins recognized by this antibody, while FIG. 10 shows that this antibody specifically detects many PKA protein substrates in a cell but will not recognize substrates of the ERK2 or CDC2 kinases, which have different substrate specificities.

EXAMPLE VIII

Phosphoantibody to the Substrate Consensus Sequence for Bulky Ring-Directed Kinases: [F/Y][T/S]* or [S/T]*F Some important classes of protein kinases are regulated by phosphorylation of a specific serine or threonine flanked by either phenylalanine or tyrosine. For example, Akt, which plays a central role in regulating cell survival, is activated by phosphorylation at Ser473, a site flanked by phenylalanine and tyrosine (D. R. Alessi et al. EMBO J. 15:6541–6551 (1996)). RSK1 (Ser381) and the PKC's also contain this consensus site, phosphorylation of which is required for their activity (K. N. Dalby et al. J. Biol. Chem. 273:1496–1505 (1998); L. M. Keranen et al. Curr. Biol. 5:1395–1403 (1995)).

To help study signaling pathways regulated by phosphorylation at these key regulatory sites we developed an antibody that detects phospho-serine and phospho-threonine only when preceded by tyrosine, tryptophan or phenylalanine or when followed by phenylalanine. This antibody was raised against the following synthetic peptide antigen, where X represents a position in the peptide synthesis where a mixture of all twenty amino acids were used and Ser* or Thr* represents phospho-serine or phospho-threonine: -X-X-X-X-F-X-X-F-[S*/T*]-[F/Y]-X-X-X-X-C (SEQ ID NO: 47). This synthetic phospho-peptide was conjugated to KLH and injected into rabbits. Test bleeds were collected and characterized by ELISA on phospho and non-phospho versions of the peptide antigen.

Once rabbits stared to show high phospho-specific titers, 40 ml production bleeds were obtained. Bleeds were dialyzed overnight in 0.025M NaAcetate, 0.01M NaCl pH=5.2 at 49° C., then spun at 11,200 rpm at 4° C. for 30min to precipitate serum lipids. Serum supernatant was then purified by Protein A chromatography on a Pharmacia (Piscataway, N.J.) ÄKTA FPLC to isolate the IgG antibody fraction. Affinity chromatography was then performed using peptide coupled to SulfoLink resin from Pierce (#20401; coupling directions according to manufacturer). Both phospho-peptide-containing resin and the corresponding non-phospho-peptide resin were prepared. Two rounds of subtractive purification were performed using the non-phospho-peptide resin: Protein A eluate was incubated with non-phospho-peptide resin by rotation in a sealed column at room temperature for one hour, in order to remove antibodies reactive with the non-phospho version of the protein antigen. The column was drained and the flow-through (containing the desired antibody) incubated with fresh non-phospho-peptide resin. The flow-through from this second subtractive step was finally positively purified by incubation with phospho-peptide resin. After the phospho-peptide column was drained and washed twice with PBS, phospho-specific antibody (bound to the resin) was-eluted with 0.1M Glycine, pH 2.7 and pooled fractions were neutralized with 1M Tris-HCl, pH 9.5 (~1–2% of fraction volume). The eluted phospho-specific antibody was then dialyzed overnight in PBS at 4° C.

Figure 11:
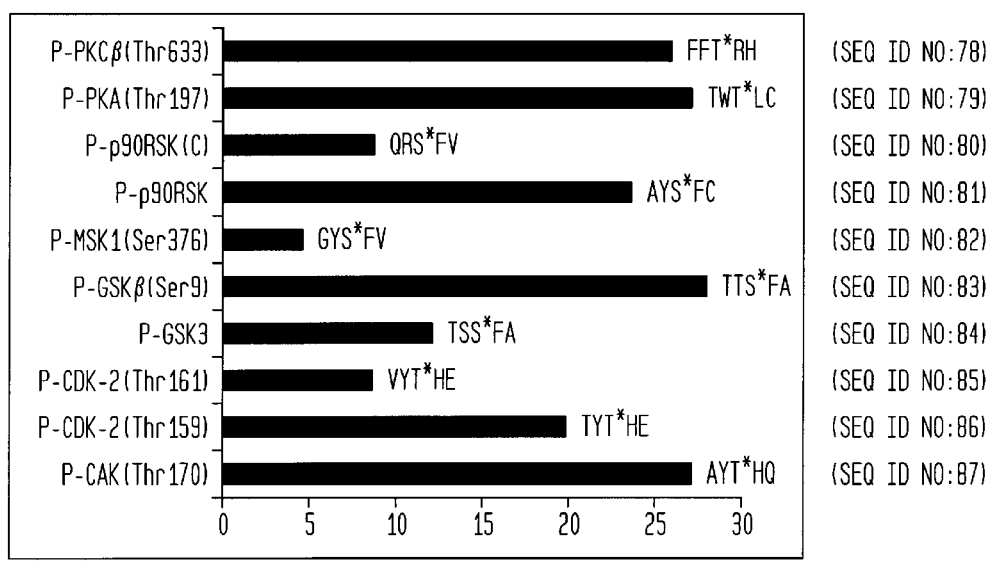
FIG. 11 shows the signal to noise ratio of ELISA reading using phospho-serine/threonine phenylalanine antibody against the peptides containing phenylalanine, tyrosine or tryptophan.
Figure 12:
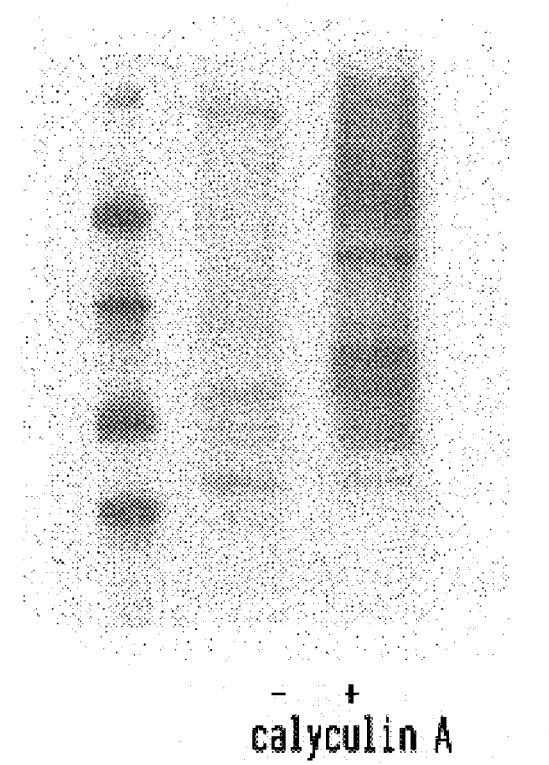
FIG. 12 is a Western analysis of calyculin A-treated A431 cells using phospho-serinine/phenylalanine substrates antibody.

The resulting antibody is highly specific for phosphorylated [F/Y][T/S]- or [S/T]F-containing peptides (FIG. 11). It does not recognize non-phosphorylated [F/Y][T/S] or [S/T]F motifs or other phospho-serine/threonine containing proteins and peptides (signal to noise ratios were determined as a ratio of reactivity with the phospho-peptide to reactivity with the corresponding non-phospho-peptide). This antibody does not recognize other phospho-threonine/serine containing motifs. FIG. 12 indicates that in mammalian cells there are many recognized by this antibody.

What is claimed is:

1. A motif-specific, context-independent antibody that specifically binds a recurring kinase consensus substrate motif or a protein-protein binding motif, said motif consisting of up to four invariant amino acids, at least one phosphorylated amino acid, and optionally, one or more variable/degenerate amino acid position(s), said antibody specifically binding said motif in a plurality of different peptides or proteins from an organism in which said motif recurs, wherein said antibody is not a site-specific antibody.

2. The antibody of claim 1, wherein said kinase consensus substrate motif is a MAPK consensus substrate motif[S] (PXS*P).

3. The antibody of claim 1, wherein said antibody is monoclonal.

4. The antibody of claim 1, wherein said antibody is polyclonal.

5. The antibody of claim 1, wherein said antibody is produced by a method comprising the steps of:
   (a) constructing a combinatorial peptide library comprising (i) a fixed motif, wherein said fixed motif comprises said kinase consensus substrate motif or said protein-protein binding motif, and (ii) a plurality of degenerate amino acids surrounding said motif;
   (b) immunizing a host with said peptide library; and
   (c) isolating antisera from said host, and purifying said motif-specific, context-independent antibody from said antisera.

6. The antibody of claim 5, wherein said method further comprises the step of utilizing spleen cells from said host of step (b) to generate at least one monoclonal, motif-specific, context-independent antibody.

7. The antibody of claim 1, wherein said kinase consensus substrate motif is a DCK consensus substrate motif (PXT*/S*PXR).

8. The antibody of claim 1, wherein said kinase consensus substrate motif is a PKA consensus substrate motif (RRXT*).

9. The antibody of claim 1, wherein said kinase consensus substrate motif is a Akt consensus substrate motif (RXRXXT*).

10. The antibody of claim 1, wherein said kinase consensus substrate motif is a bulky ring-directed kinase consensus substrate motif ([F/Y][T*/S*] or [S/T*][F]).

11. The antibody of claim 1, wherein said kinase protein-protein binding motif is a 14-3-3 binding motif (RSXS*XP).

* * * * *

SEQUENCE LISTING

<160> NUMBER OF SEQ ID NOS: 87

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION; threonine at position 9 is
      phosphorylated

<400> SEQUENCE: 1

```
Ile Lys Asp Gly Ala Thr Met Lys Thr Phe Cys Gly Thr Pro
1               5                   10
```

<210> SEQ ID NO 2
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; threonine at position 5 is
      phosphorylated

<400> SEQUENCE: 2

```
Asp Ala Ala Val Thr Pro Lys Lys Arg His Leu Ser Lys Cys
1               5                   10
```

<210> SEQ ID NO 3
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; threonine at position 8 is
      phosphorylated

<400> SEQUENCE: 3

```
Asp Thr Gln Ile Lys Arg Asn Thr Phe Val Gly Thr Pro Phe Cys
1               5                   10                  15
```

<210> SEQ ID NO 4
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; threonine at position 5 is
      phosphorylated

<400> SEQUENCE: 4

```
His Gln Val Val Thr Arg Trp Tyr Arg Cys
1               5                   10
```

<210> SEQ ID NO 5
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; threonine at position 7 is
      phosphorylated

<400> SEQUENCE: 5

```
His Gln Val Leu Met Lys Thr Val Cys Gly
1               5                   10
```

<210> SEQ ID NO 6
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; threonine at position 7 is
      phosphorylated

<400> SEQUENCE: 6

```
Ile Pro Ile Arg Val Tyr Thr His Glu Val Val Thr Leu Cys
1               5                   10
```

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; threonine at position 8 is
      phosphorylated

<400> SEQUENCE: 7

```
Gly Val Pro Val Arg Thr Tyr Thr His Glu Val Val Thr Leu Cys
1               5                   10                  15
```

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; threonine at position 8 is
      phosphorylated

<400> SEQUENCE: 8

```
Asn Gln Val Phe Leu Gly Phe Thr Tyr Val Ala Pro Lys Lys Cys
1               5                   10                  15
```

<210> SEQ ID NO 9
<211> LENGTH: 14
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION; threonine at position 12 is
      phosphorylated

<400> SEQUENCE: 9

```
Lys Glu His Met Met Asp Gly Val Thr Thr Arg Thr Phe Cys
1               5                   10
```

<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; threonine at position 7 is
      phosphorylated
<221> NAME/KEY: MOD_RES
<222> LOCATION: (9)..(9)
<223> OTHER INFORMATION: PHOSPHORYLATION; tyrosine at position 9 is
      phosphorylated

<400> SEQUENCE: 10

```
Asp His Thr Gly Phe Leu Thr Glu Tyr Val Ala Thr Arg Trp Cys
1               5                   10                  15
```

<210> SEQ ID NO 11
<211> LENGTH: 15
<212> TYPE: PRT
<213> ORGANISM: Homo sapiens
<220> FEATURE:
<221> NAME/KEY: MOD_RES

```
<222> LOCATION: (5)..(5)
<223> OTHER INFORMATION: PHOSPHORYLATION; threonine at position 5 is
      phosphorylated
<221> NAME/KEY: MOD_RES
<222> LOCATION: (9)..(9)
<223> OTHER INFORMATION: PHOSPHORYLATION; serine at position 9 is
      phosphorylated

<400> SEQUENCE: 11

Glu Leu Leu Pro Thr Pro Pro Leu Ser Pro Ser Arg Arg Ser Cys
1               5                   10                  15

<210> SEQ ID NO 12
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; threonine at position 10 is
      phosphorylated
<221> NAME/KEY: MOD_RES
<222> LOCATION: (12)..(12)
<223> OTHER INFORMATION: PHOSPHORYLATION; tyrosine at position 12 is
      phosphorylated

<400> SEQUENCE: 12

Leu Ala Arg His Thr Asp Asp Glu Met Thr Gly Tyr Val Ala Thr Arg
1               5                   10                  15
Cys

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION; threonine at position 5 is
      phosphorylated
<221> NAME/KEY: MOD_RES
<222> LOCATION: (7)..(7)
<223> OTHER INFORMATION: PHOSPHORYLATION; tyrosine at position 7 is
      phosphorylated

<400> SEQUENCE: 13

Ser Phe Met Met Thr Pro Tyr Val Val Thr Arg Tyr Tyr Arg Cys
1               5                   10                  15

<210> SEQ ID NO 14
<211> LENGTH: 14
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is phosphoserine or
      phosphothreonine
<221> NAME/KEY: MISC_FEATURE
<222> LOCATION: (11)..(11)
<223> OTHER INFORMATION: Xaa at position 11 is arginine or lysine
<221> NAME/KEY: MISC_FEATURE
<222> LOCATION: (1)..(14)
<223> OTHER INFORMATION: Xaa at positions 1-5, 7, 10, and 12-14  = any
      one of the 20 amino acids except cysteine

<400> SEQUENCE: 14

Xaa Xaa Xaa Xaa Xaa Pro Xaa Xaa Pro Xaa Xaa Xaa Xaa Xaa
1               5                   10

<210> SEQ ID NO 15
```

```
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION;  serine at position 8 is
      phosphorylated
<221> NAME/KEY: MISC_FEATURE
<222> LOCATION: (1)..(14)
<223> OTHER INFORMATION: Xaa at positions 1-4, 7, 9, and 11-14 = any
      one of the 20 amino acids except cysteine

<400> SEQUENCE: 15

Xaa Xaa Xaa Xaa Arg Ser Xaa Ser Xaa Pro Xaa Xaa Xaa Xaa
1               5                   10

<210> SEQ ID NO 16
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: Xaa at positions 1-4, 7, 9, and 11-14 = any one
      of the 20 amino acids except cysteine

<400> SEQUENCE: 16

Xaa Xaa Xaa Xaa Arg Ser Xaa Ser Xaa Pro Xaa Xaa Xaa Xaa
1               5                   10

<210> SEQ ID NO 17
<211> LENGTH: 14
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is phosphoserine or
      phosphothreonine
<221> NAME/KEY: MISC_FEATURE
<222> LOCATION: (1)..(14)
<223> OTHER INFORMATION: Xaa at positions 1-5, 7, and 10-14 = any one of
      the 20 amino acids except cysteine

<400> SEQUENCE: 17

Xaa Xaa Xaa Xaa Xaa Pro Xaa Xaa Pro Xaa Xaa Xaa Xaa Xaa
1               5                   10

<210> SEQ ID NO 18
<211> LENGTH: 14
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is serine or threonine
<221> NAME/KEY: MISC_FEATURE
<222> LOCATION: (1)..(14)
<223> OTHER INFORMATION: Xaa at positions 1-5, 7, and 10-14 = any one of
      the 20 amino acids except cysteine

<400> SEQUENCE: 18

Xaa Xaa Xaa Xaa Xaa Pro Xaa Xaa Pro Xaa Xaa Xaa Xaa Xaa
1               5                   10

<210> SEQ ID NO 19
<211> LENGTH: 14
<212> TYPE: PRT
<213> ORGANISM: Homo sapiens
<220> FEATURE:
```

```
<221> NAME/KEY: MISC_FEATURE
<222> LOCATION: (5)..(5)
<223> OTHER INFORMATION: Xaa at position 5 is aspartic acid or glutamic
      acid
<221> NAME/KEY: MISC_FEATURE
<222> LOCATION: (8)..(8)
<223> OTHER INFORMATION: Xaa at position 8  is phosphoserine or
      phosphothreonine
<221> NAME/KEY: MISC_FEATURE
<222> LOCATION: (1)..(14)
<223> OTHER INFORMATION: Xaa at positions 1-4, 6-7, and 9-13 = any one
      of the 20 amino acids except cysteine

<400> SEQUENCE: 19

Xaa Xaa Xaa Xaa Xaa Xaa Xaa Xaa Xaa Xaa Xaa Xaa Xaa Cys
1               5                   10

<210> SEQ ID NO 20
<211> LENGTH: 13
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is phosphoserine or
      phosphothreonine
<221> NAME/KEY: MISC_FEATURE
<222> LOCATION: (8)..(10)
<223> OTHER INFORMATION: Xaa at positions 8-10 is aspartic acid or
      glutamic acid
<221> NAME/KEY: MISC_FEATURE
<222> LOCATION: (1)..(13)
<223> OTHER INFORMATION: Xaa at positions 1-6, and 11-13 = any one of
      the 20 amino acids except cysteine

<400> SEQUENCE: 20

Xaa Xaa Xaa Xaa Xaa Xaa Xaa Xaa Xaa Xaa Xaa Xaa Xaa
1               5                   10

<210> SEQ ID NO 21
<211> LENGTH: 15
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa at position 9 is phosphoserine or
      phosphothreonine
<221> NAME/KEY: MISC_FEATURE
<222> LOCATION: (10)..(10)
<223> OTHER INFORMATION: Xaa at position 10 is phenylalanine or tyrosine
<221> NAME/KEY: MISC_FEATURE
<222> LOCATION: (1)..(14)
<223> OTHER INFORMATION: Xaa at positions 1-4, 6-7, and 11-14 =  any one
      of the 20 amino acids except cysteine

<400> SEQUENCE: 21

Xaa Xaa Xaa Xaa Phe Xaa Xaa Phe Xaa Xaa Xaa Xaa Xaa Xaa Cys
1               5                   10                  15

<210> SEQ ID NO 22
<211> LENGTH: 14
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is arginine or lysine
<221> NAME/KEY: MISC_FEATURE
<222> LOCATION: (7)..(7)
<223> OTHER INFORMATION: Xaa at position 7 is phosphoserine or
      phosphothreonine
<221> NAME/KEY: MISC_FEATURE
```

```
<222> LOCATION: (1)..(13)
<223> OTHER INFORMATION: Xaa at positions 1-4, 6, and 8-13 =  any one of
      the 20 amino acids except cysteine

<400> SEQUENCE: 22

Xaa Xaa Xaa Xaa Xaa Xaa Xaa Xaa Xaa Xaa Xaa Xaa Xaa Cys
1               5                  10

<210> SEQ ID NO 23
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is phosphoserine or
      phosphothreonine
<221> NAME/KEY: MISC_FEATURE
<222> LOCATION: (4)..(4)
<223> OTHER INFORMATION: Xaa at position 4 is arginine or lysine
<221> NAME/KEY: MISC_FEATURE
<222> LOCATION: (1)..(13)
<223> OTHER INFORMATION: Xaa at positions 1-3, 5-6, and 8-13 = any one
      of the 20 amino acids except cysteine

<400> SEQUENCE: 23

Xaa Xaa Xaa Xaa Xaa Xaa Xaa Xaa Xaa Xaa Xaa Xaa Xaa Cys
1               5                  10

<210> SEQ ID NO 24
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is phosphoserine or
      phosphothreonine
<221> NAME/KEY: MISC_FEATURE
<222> LOCATION: (8)..(8)
<223> OTHER INFORMATION: Xaa at position 8 is phenylalanine or
      isoleucine or methionine
<221> NAME/KEY: MISC_FEATURE
<222> LOCATION: (1)..(13)
<223> OTHER INFORMATION: Xaa at positions 1-6, and 9-13 = any one of the
      20 amino acids except cysteine

<400> SEQUENCE: 24

Xaa Xaa Xaa Xaa Xaa Xaa Xaa Xaa Xaa Xaa Xaa Xaa Xaa Cys
1               5                  10

<210> SEQ ID NO 25
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is phosphoserine or
      phosphothreonine
<221> NAME/KEY: MISC_FEATURE
<222> LOCATION: (8)..(8)
<223> OTHER INFORMATION: Xaa at position 8 is phenylalanine or
      isoleucine
<221> NAME/KEY: MISC_FEATURE
<222> LOCATION: (1)..(13)
<223> OTHER INFORMATION: Xaa at positions 1-6, and 9-13 = any one of the
      20 amino acids except cysteine

<400> SEQUENCE: 25

Xaa Xaa Xaa Xaa Xaa Xaa Xaa Xaa Xaa Xaa Xaa Xaa Xaa Cys
1               5                  10
```

```
<210> SEQ ID NO 26
<211> LENGTH: 15
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is phosphoserine or
      phosphothreonine
<221> NAME/KEY: MISC_FEATURE
<222> LOCATION: (1)..(14)
<223> OTHER INFORMATION: Xaa at positions 1-6, and 9-14= any one of the
      20 amino acids except cysteine

<400> SEQUENCE: 26

Xaa Xaa Xaa Xaa Xaa Xaa Xaa Pro Xaa Xaa Xaa Xaa Xaa Xaa Cys
1               5                   10                  15

<210> SEQ ID NO 27
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is phosphoserine or
      phosphothreonine
<221> NAME/KEY: MISC_FEATURE
<222> LOCATION: (1)..(14)
<223> OTHER INFORMATION: Xaa at positions 1-5, 7, and 10-14 = any one of
      the 20 amino acids except cysteine

<400> SEQUENCE: 27

Xaa Xaa Xaa Xaa Xaa Pro Xaa Xaa Pro Xaa Xaa Xaa Xaa Xaa Cys
1               5                   10                  15

<210> SEQ ID NO 28
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is serine or threonine
<221> NAME/KEY: MISC_FEATURE
<222> LOCATION: (1)..(13)
<223> OTHER INFORMATION: Xaa at positions 1-6, and 8-13 = any one of the
      20 amino acids except cysteine

<400> SEQUENCE: 28

Xaa Xaa Xaa Xaa Xaa Xaa Xaa Xaa Xaa Xaa Xaa Xaa Xaa Cys
1               5                   10

<210> SEQ ID NO 29
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is phosphoserine or
      phosphothreonine
<221> NAME/KEY: MISC_FEATURE
<222> LOCATION: (11)..(11)
<223> OTHER INFORMATION: Xaa at position 11 is arginine or lysine
<221> NAME/KEY: MISC_FEATURE
<222> LOCATION: (1)..(14)
<223> OTHER INFORMATION: Xaa at positions 1-5, 7, 10, and 12-14 = any
      one of the 20 amino acids except cysteine

<400> SEQUENCE: 29
```

```
Xaa Xaa Xaa Xaa Xaa Pro Xaa Xaa Pro Xaa Xaa Xaa Xaa Xaa Cys
1               5                   10                  15
```

<210> SEQ ID NO 30
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION;  threonine at position 6 is
      phosphorylated

<400> SEQUENCE: 30

```
Val Ile Pro Pro His Thr Pro Val Arg Thr Val Met Asn Thr Cys
1               5                   10                  15
```

<210> SEQ ID NO 31
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION;  threonine at position 5 is
      phosphorylated

<400> SEQUENCE: 31

```
Ser Val Ala Lys Thr Met Asp Ala Gly Cys
1               5                   10
```

<210> SEQ ID NO 32
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; threonine at position 10 is
      phosphorylated

<400> SEQUENCE: 32

```
Arg Ile Tyr Ser Tyr Gln Met Ala Leu Thr Pro Val Val Val Lys Cys
1               5                   10                  15
```

<210> SEQ ID NO 33
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; serine at position 8 is
      phosphorylated
<221> NAME/KEY: MISC_FEATURE
<222> LOCATION: (1)..(14)
<223> OTHER INFORMATION: Xaa at positions 1-4, 7, 9, and 11-14 = any one
      of the 20 amino acids except cysteine

<400> SEQUENCE: 33

```
Xaa Xaa Xaa Xaa Arg Ser Xaa Ser Xaa Pro Xaa Xaa Xaa Xaa Cys
1               5                   10                  15
```

<210> SEQ ID NO 34
<211> LENGTH: 15
<212> TYPE: PRT
<213> ORGANISM: Homo sapiens
<220> FEATURE:
<221> NAME/KEY: MISC_FEATURE

```
<222> LOCATION: (1)..(14)
<223> OTHER INFORMATION: Xaa at positions 1-4, 7, 9, and 11-14 = any one
      of the 20 amino acids except cysteine

<400> SEQUENCE: 34

Xaa Xaa Xaa Xaa Arg Ser Xaa Ser Xaa Pro Xaa Xaa Xaa Xaa Cys
1               5                   10                  15

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION;  serine at position 7 is
      phosphorylated

<400> SEQUENCE: 35

Gly Leu Tyr Arg Ser Pro Ser Met Pro Glu Asn Leu Asn Arg Cys
1               5                   10                  15

<210> SEQ ID NO 36
<211> LENGTH: 15
<212> TYPE: PRT
<213> ORGANISM: Homo sapiens

<400> SEQUENCE: 36

Gly Leu Tyr Arg Ser Pro Ser Met Pro Glu Asn Leu Asn Arg Cys
1               5                   10                  15

<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION; serine at position 7 is
      phosphorylated

<400> SEQUENCE: 37

Thr Arg Ser Arg His Ser Ser Tyr Pro Ala Gly Thr Glu Glu Cys
1               5                   10                  15

<210> SEQ ID NO 38
<211> LENGTH: 15
<212> TYPE: PRT
<213> ORGANISM: Homo sapiens

<400> SEQUENCE: 38

Thr Arg Ser Arg His Ser Ser Tyr Pro Ala Gly Thr Glu Glu Cys
1               5                   10                  15

<210> SEQ ID NO 39
<211> LENGTH: 15
<212> TYPE: PRT
<213> ORGANISM: Homo sapiens

<400> SEQUENCE: 39

Phe Arg Gly Arg Ser Arg Ser Ala Pro Pro Asn Leu Trp Ala Cys
1               5                   10                  15

<210> SEQ ID NO 40
<211> LENGTH: 15
<212> TYPE: PRT
<213> ORGANISM: Homo sapiens
```

```
<220> FEATURE:
<221> NAME/KEY: MOD_RES
<222> LOCATION: (7)..(7)
<223> OTHER INFORMATION: PHOSPHORYLATION; serine at position 7 is
      phosphorylated

<400> SEQUENCE: 40

Phe Arg Gly Arg Ser Arg Ser Ala Pro Pro Asn Leu Trp Ala Cys
1               5                   10                  15

<210> SEQ ID NO 41
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is serine or threonine
<221> NAME/KEY: MISC_FEATURE
<222> LOCATION: (1)..(14)
<223> OTHER INFORMATION: Xaa at positions 1-5, 7, and 10-14 = any one of
      the 20 amino acids except cysteine

<400> SEQUENCE: 41

Xaa Xaa Xaa Xaa Xaa Pro Xaa Xaa Pro Xaa Xaa Xaa Xaa Xaa Cys
1               5                   10                  15

<210> SEQ ID NO 42
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is phosphoserine or
      phosphothreonine
<221> NAME/KEY: MISC_FEATURE
<222> LOCATION: (11)..(11)
<223> OTHER INFORMATION: Xaa at position 11 is arginine or lysine
<221> NAME/KEY: MISC_FEATURE
<222> LOCATION: (1)..(14)
<223> OTHER INFORMATION: Xaa at positions 1-5, 7, 10, and 12-14 = any
      one of the 20 amino acids except cysteine

<400> SEQUENCE: 42

Xaa Xaa Xaa Xaa Xaa Pro Xaa Xaa Pro Xaa Xaa Xaa Xaa Xaa Cys
1               5                   10                  15

<210> SEQ ID NO 43
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 43

Ser Pro Tyr Lys Phe Pro Ser Ser Pro Leu Arg Ile Pro Gly Cys
1               5                   10                  15

<210> SEQ ID NO 44
<211> LENGTH: 15
<212> TYPE: PRT
<213> ORGANISM: Homo sapiens

<400> SEQUENCE: 44

Val Ile Pro Pro His Thr Pro Val Arg Thr Val Met Asn Thr Cys
1               5                   10                  15
```

```
<210> SEQ ID NO 45
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; threonine at position 10 is
      phosphorylated
<221> NAME/KEY: MISC_FEATURE
<222> LOCATION: (2)..(14)
<223> OTHER INFORMATION: Xaa at positions 2-4, 6, 8-9, 11-14 = any one
      of the 20 amino acids except cysteine

<400> SEQUENCE: 45

Cys Xaa Xaa Xaa Arg Xaa Arg Xaa Xaa Thr Xaa Xaa Xaa Xaa
1               5                   10

<210> SEQ ID NO 46
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION; threonine at position 10 is
      phosphorylated
<221> NAME/KEY: MISC_FEATURE
<222> LOCATION: (2)..(14)
<223> OTHER INFORMATION: Xaa at positions 2-6, 9, and 11-14 = any one of
      the 20 amino acids except cysteine

<400> SEQUENCE: 46

Cys Xaa Xaa Xaa Xaa Xaa Arg Arg Xaa Thr Xaa Xaa Xaa Xaa
1               5                   10

<210> SEQ ID NO 47
<211> LENGTH: 15
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa at position 9 is phosphoserine or
      phosphothreonine
<221> NAME/KEY: MISC_FEATURE
<222> LOCATION: (10)..(10)
<223> OTHER INFORMATION: Xaa at position 10 is phenylalanine or tyrosine
<221> NAME/KEY: MISC_FEATURE
<222> LOCATION: (1)..(14)
<223> OTHER INFORMATION: Xaa at positions 1-4, 6-7, and 11-14 = any one
      of the 20 amino acids except cysteine

<400> SEQUENCE: 47

Xaa Xaa Xaa Xaa Phe Xaa Xaa Phe Xaa Xaa Xaa Xaa Xaa Xaa Cys
1               5                   10                  15

<210> SEQ ID NO 48
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 48

Arg Gln Arg Ser Thr Ser Thr Pro
1               5
```

```
<210> SEQ ID NO 49
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 49

Lys Gly Arg Thr Trp Thr Leu Cys
1               5

<210> SEQ ID NO 50
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 50

Arg Pro Arg Thr Thr Ser Phe Ala
1               5

<210> SEQ ID NO 51
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 51

Arg Arg Arg Thr Ser Ser Phe Ala
1               5

<210> SEQ ID NO 52
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 52

Arg Arg Arg Ala Ala Ser Met Asp
1               5

<210> SEQ ID NO 53
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 53

Arg Ile Arg Thr Gln Ser Phe Ser
```

```
<210> SEQ ID NO 54
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 54

Arg Glu Arg Lys Arg Thr Val Trp
1               5

<210> SEQ ID NO 55
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 55

Lys Asp Arg Gln Gly Thr His Lys
1               5

<210> SEQ ID NO 56
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 56

Arg Asp Arg Asn Gly Thr His Leu
1               5

<210> SEQ ID NO 57
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 57

Lys Leu Arg Leu Ser Thr Asp Tyr
1               5

<210> SEQ ID NO 58
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 58
```

Arg Asp Lys Ser Val Thr Asp Ser
1               5

<210> SEQ ID NO 59
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 59

Arg Leu Arg Lys Ser Ser Ser Tyr
1               5

<210> SEQ ID NO 60
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; threonine at position 6 is
      phosphorylated

<400> SEQUENCE: 60

Arg Pro Arg Ser Cys Thr Trp Pro
1               5

<210> SEQ ID NO 61
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION; serine at position 6 is
      phosphorylated

<400> SEQUENCE: 61

Arg Arg Arg Ala Ala Ser Met Asp
1               5

<210> SEQ ID NO 62
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 62

Arg Phe Phe Thr Arg
1               5

<210> SEQ ID NO 63
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 63

Arg Thr Tyr Thr Leu
1               5

<210> SEQ ID NO 64
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 64

Lys Arg Ser Thr Met
1               5

<210> SEQ ID NO 65
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; serine at position 4 is
      phosphorylated

<400> SEQUENCE: 65

Arg Arg Arg Ser Ser
1               5

<210> SEQ ID NO 66
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; serine at position 4 is
      phosphorylated

<400> SEQUENCE: 66

Arg Arg Pro Ser Tyr
1               5

<210> SEQ ID NO 67
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 67

Arg Thr Tyr Thr His
1               5

<210> SEQ ID NO 68
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; serine at position 4 is
      phosphorylated

```
<400> SEQUENCE: 68

Arg Ser Pro Ser Met
1               5

<210> SEQ ID NO 69
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 69

Arg Lys Arg Thr Val
1               5

<210> SEQ ID NO 70
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 70

Arg Gln Gly Thr His
1               5

<210> SEQ ID NO 71
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 71

Arg Ser Leu Thr Glu
1               5

<210> SEQ ID NO 72
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 72

Arg Gln Glu Thr Val
1               5

<210> SEQ ID NO 73
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated
```

```
<400> SEQUENCE: 73

Arg Ala Tyr Thr His
1               5

<210> SEQ ID NO 74
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 74

Lys Arg Asp Thr Phe
1               5

<210> SEQ ID NO 75
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 75

Lys Ser Val Thr Asp
1               5

<210> SEQ ID NO 76
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; serine at position 4 is
      phosphorylated

<400> SEQUENCE: 76

Arg Lys Ser Ser Ser
1               5

<210> SEQ ID NO 77
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION; threonine at position 4 is
      phosphorylated

<400> SEQUENCE: 77

Arg Ser Cys Thr Tyr
1               5

<210> SEQ ID NO 78
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; threonine at position 3 is
``` phosphorylated

<400> SEQUENCE: 78

Phe Phe Thr Arg His
1               5

<210> SEQ ID NO 79
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; threonine at position 3 is
      phosphorylated

<400> SEQUENCE: 79

Thr Trp Thr Leu Cys
1               5

<210> SEQ ID NO 80
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; serine at position 3 is
      phosphorylated

<400> SEQUENCE: 80

Gln Arg Ser Phe Val
1               5

<210> SEQ ID NO 81
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; serine at position 3 is
      phosphorylated

<400> SEQUENCE: 81

Ala Tyr Ser Phe Cys
1               5

<210> SEQ ID NO 82
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; serine at position 3 is
      phosphorylated

<400> SEQUENCE: 82

Gly Tyr Ser Phe Val
1               5

<210> SEQ ID NO 83
<211> LENGTH: 5
<212> TYPE: PRT
<213> ORGANISM: Homo sapiens
<220> FEATURE:
<221> NAME/KEY: MOD_RES
<222> LOCATION: (3)..(3)

-continued

```
<223> OTHER INFORMATION: PHOSPHORYLATION; serine at position 3 is
      phosphorylated

<400> SEQUENCE: 83

Thr Thr Ser Phe Ala
1               5

<210> SEQ ID NO 84
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; serine at position 3 is
      phosphorylated

<400> SEQUENCE: 84

Thr Ser Ser Phe Ala
1               5

<210> SEQ ID NO 85
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; threonrine at position 3 is
      phosphorylated

<400> SEQUENCE: 85

Val Tyr Thr His Glu
1               5

<210> SEQ ID NO 86
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; threonrine at position 3 is
      phosphorylated

<400> SEQUENCE: 86

Thr Tyr Thr His Glu
1               5

<210> SEQ ID NO 87
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION; threonrine at position 3 is
      phosphorylated

<400> SEQUENCE: 87

Ala Tyr Thr His Gln
1               5
```